United States Patent
Xi et al.

(10) Patent No.: US 8,569,476 B2
(45) Date of Patent: Oct. 29, 2013

(54) METHOD FOR PREPARING OLIGONUCLEOTIDE

(75) Inventors: Zhen Xi, Tianjin (CN); Jinyu Huang, Tianjin (CN); Junbin Zhang, Tianjin (CN)

(73) Assignee: Suzhou Ribo Life Science Co., Ltd., Jiangsu (CN)

( * ) Notice: Subject to any disclaimer, the term of this patent is extended or adjusted under 35 U.S.C. 154(b) by 262 days.

(21) Appl. No.: 13/003,195

(22) PCT Filed: Sep. 22, 2009

(86) PCT No.: PCT/CN2009/074101
§ 371 (c)(1),
(2), (4) Date: Jan. 7, 2011

(87) PCT Pub. No.: WO2010/037326
PCT Pub. Date: Apr. 8, 2010

(65) Prior Publication Data
US 2011/0237786 A1    Sep. 29, 2011

(30) Foreign Application Priority Data

Sep. 23, 2008  (CN) .......................... 2008 1 0149372

(51) Int. Cl.
*C07H 21/02* (2006.01)
*C07H 21/00* (2006.01)

(52) U.S. Cl.
USPC .................... 536/25.3; 536/25.31; 536/25.33

(58) Field of Classification Search
None
See application file for complete search history.

(56) References Cited

FOREIGN PATENT DOCUMENTS

| | | |
|---|---|---|
| CN | 1245809 | 3/2000 |
| CN | 1409719 | 4/2003 |
| CN | 101133073 | 2/2008 |
| DE | DD273064 | 11/1989 |
| WO | 0127126 | 4/2001 |
| WO | 2006094963 | 9/2006 |

OTHER PUBLICATIONS (R) Khorana, H. G., "Chemical Synthesis of Polynucleotides," Ch. 5 in "Some Recent Developments in the Chemistry of Phosphate Esters of Biological Interest," New York, NY, 1961, John Wiley & Sons, Inc., only pp. 93-125 supplied.*
(S) Efimov et al., "Synthesis of RNA by the Rapid Phosphotriester Method Using Azido-Based 2'-O-Protecting Groups," Nucleosides, Nucleotides & Nucleic Acids, 28(9), 846-865 (Sep., 2009); only abstract supplied.*
(T) Anon., "Aldrich Handbook 2005-2006," Sigma-Aldrich Corporation, 2005, Milwaukee, WI, only p. 1524 supplied: see col. 2, 5th entry, wherein MSNT is listed as a "[c]oupling reagent for oligonucleotide synthesis.".*

Wang et al., "Textbook Series of 21st Century, DNA" Higher Education Press, Book 1, Edition 3.

* cited by examiner

Primary Examiner — Lawrence E Crane
(74) Attorney, Agent, or Firm — Volpe and Koenig, P.C.

(57) ABSTRACT

A method for preparing oligonucleotide comprising reacting the compound of Formula (1) with the compound of Formula (2) in a liquid reaction medium under the condition of condensation reaction to obtain the compound of formula (3) is provided. 1-(2-mesitylenesulfonyl)-3-nitro-1H-1,2,4-triazole (MSNT) is applied as condensing agent. Oligonucleotides synthesized in the liquid reaction medium could be obtained on a large scale.

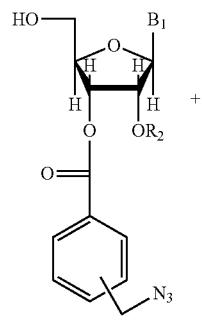

Formula (1)

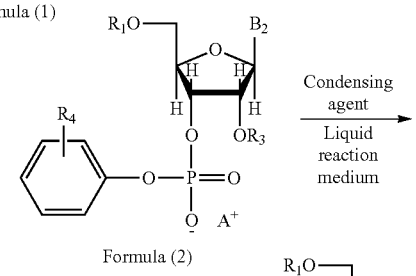

Formula (2)

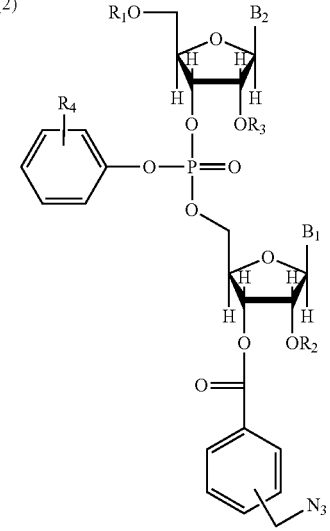

Formula (3)

11 Claims, No Drawings

METHOD FOR PREPARING OLIGONUCLEOTIDE

CROSS-REFERENCE TO RELATED APPLICATIONS

The present application claims the benefit of priority from Chinese patent application CN200810149372.5, filed on Sep. 23, 2008, entitled "A Method for Preparing Oligonucleotide", which is incorporated herein by reference in its entirety.

The Sequence Listing created and filed on Mar. 7, 2013, and having a file size of 1,605 bytes is incorporated herein by reference as if fully set forth.

This application is a 35 U.S.C. §371 national phase application of PCT/CN2009/074101, which is incorporated herein by reference as if fully set forth.

FIELD OF THE INVENTION

The present invention relates to a method for preparing oligonucleotide.

BACKGROUND OF THE INVENTION

The basic structural unit of oligonucleotide is nucleotide which comprises base, pentose and phosphoric acid. Nucleotides may be classified into RNA (ribonucleic acid) and DNA (deoxyribonucleic acid) which have the same basic chemical structure, except that they contain different pentose in which the pentose of RNA is D-ribose, and the pentose of DNA is D-2-deoxyribose. The base generally includes guanine, adenine, cytosine, thymine and uracil. The chemical synthesis method of oligonucleotides currently widely adopted is solid phase synthesis method (also known as phosphoramidite-triester method). At pages 520-521 of the Biochemistry (Book 1, Edition 3, Wang Jingyan et al, Higher Education Press), the principle of solid phase synthesis is introduced as follows: All reactions take place in a solid phase column which has a small synthesis scale. Firstly, some free groups on the nucleotides to be activated are protected (blocked) to make the reactions go towards the designed direction. 5'-OH is protected with DMTr (4,4'-dimethoxytriphenylmethyl) group, and the amino groups on the base are protected with benzoyl groups. 3'-OH is activated with amino phosphorous acid compound. The 3'-OH of the first nucleotide is combined with the solid phase (resin). A phosphite triester is formed between its 5'-OH and the activated monomer (nucleotide). As the 5'-OH on the activated monomer and the amino group on the base are protected, they won't participate in the reaction. During the reaction in the second step, phosphite triester is oxidized by iodine into phosphate triester; during the reaction in the third step, trichloroacetic acid is added to remove protective agent DMTr on 5'-OH in the growing chain. By now, DNA chain has been extended by one more nucleotide unit and is ready for the reactions for next round of extension. According to the program input in advance, after the synthesis of a whole DNA fragment is completed, thiophenol is applied to remove the protective agent DMTr on 5'-OH, and concentrated ammonium hydroxide is applied to disconnect DNA fragment from the solid phase resin so that DNA is eluted. Then concentrated ammonium hydroxide is applied again to remove the protective agent on the base under heated condition. Finally ammonium hydroxide is removed under vacuum.

As the whole process of the foregoing solid phase synthesis is conducted in a solid phase column, due to the limitation of the volume of the solid phase column, this method has a small synthesis scale and low yield and can't meet the requirement of mass synthesis. Following the deepening of the research on nucleic acid, on the one hand, the amount of the oligomeric RNA applied in scientific research increases rapidly, and on the other hand, the clinical application of RNA is in the ascendant, so it is a matter of significance to design a method for synthesizing RNA on a large scale.

SUMMARY OF THE INVENTION

The object of the present invention is to overcome the shortcoming of the existing chemical synthesis method of oligonucleotides—small synthesis scale and provide a method to synthesize oligonucleotide on a large scale.

The present invention provides a method for preparing oligonucleotide, comprising reacting the compound represented by Formula (1) with the compound represented by Formula (2) in a liquid reaction medium under the condition of condensation reaction to obtain the compound represented by Formula (3),

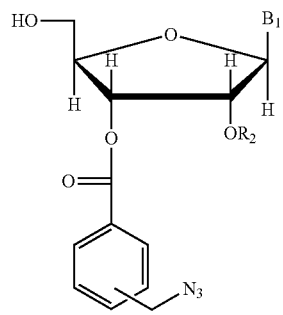

Formula (1)

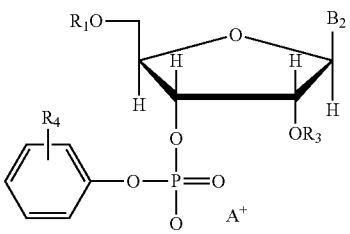

Formula (2)

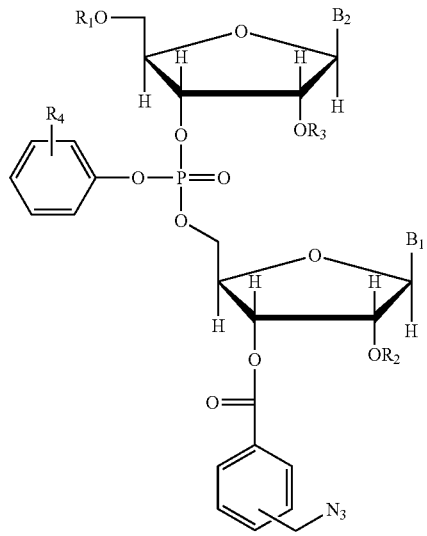

Formula (3)

wherein: $R_1$ represents 4,4'-dimethoxytriphenylmethyl (DMTr), or a covalently attached 5'-substituent derived from RNA or from DNA;

$R_2$ and $R_3$ independently represent a sterically hindered trisubstituted silyl protective group;

$R_4$ represents a halogen atom;

$A^+$ represents a tri-alkyl ammonium ion;

$B_1$ and $B_2$ independently represent 9-guaninyl substituted with N-acyl, 9-adeninyl substituted with N-acyl, 1-cytosinyl substituted with N-acyl, 1-cytosinyl or 1-uracilyl.

The method provided by the present invention adopts appropriate protective groups to protect corresponding functional groups, such that only the 5'-OH to which the compound represented by Formula (1) needs to be connected and the 3'-phosphate to which the compound represented by Formula (2) needs to be connected are exposed. The condensation reaction takes place in the liquid reaction medium to connect OH-component and P-component and obtain DNA or RNA short chains. If necessary, after this step is completed, the 5'-protective groups of the newly obtained DNA or RNA short chains may be removed, condensation reaction with the new compound represented by Formula (2) may take place again to obtain longer chains, the reaction is repeated several times and finally all protective groups are removed such that the oligonucleotides with the needed length are obtained; alternatively, the 3'-protective group of the newly obtained DNA or RNA short chains may be removed, then 3'-hydroxyl phosphate is esterified to generate a new P-component (the reaction shown in Reaction Scheme III), it again takes condensation reaction with the new compound represented by Formula (3) to obtain longer chains, the reaction is repeated several times and finally all protective groups are removed such that the expected oligonucleotides are obtained. The method provided by the present invention doesn't need a solid phase column and the reactions may take place in a liquid reaction medium, so oligonucleotides can be synthesized on a large scale.

DETAILED DESCRIPTION OF THE EMBODIMENTS

The method for preparing oligonucleotide according to the present invention comprises reacting the compound represented by Formula (1) with the compound represented by Formula (2) in a liquid reaction medium under the condition of condensation reaction to obtain the compound represented by Formula (3),

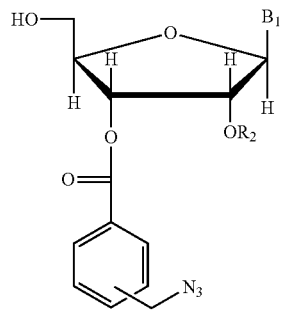

Formula (1)

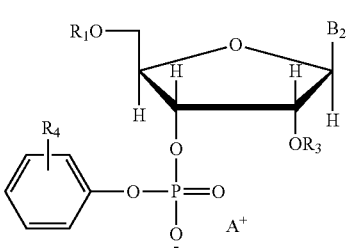

Formula (2)

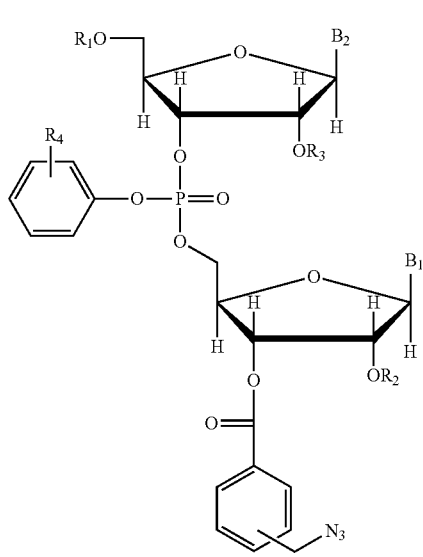

Formula (3)

wherein: $R_1$ represents 4,4'-dimethoxytriphenylmethyl, or a covalently attached 5'-substituent derived from RNA or from DNA;

$R_2$ and $R_3$ independently represent a sterically hindered trisubstituted silyl protective group;

$R_4$ represents a halogen atom;

$A^+$ represents a tri-alkyl ammonium ion;

$B_1$ and $B_2$ independently represent 9-guaninyl substituted with N-acyl, 9-adeninyl substituted with N-acyl, 1-cytosinyl substituted with N-acyl, 1-thyminyl or 1-uracilyl.

This step may be represented by Reaction Scheme I:

Reaction Scheme I

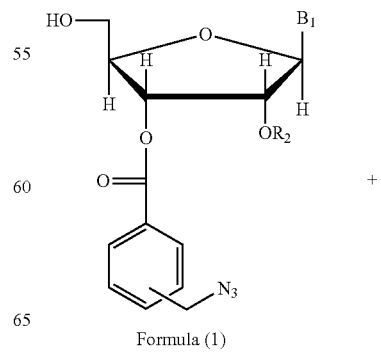

Formula (1)

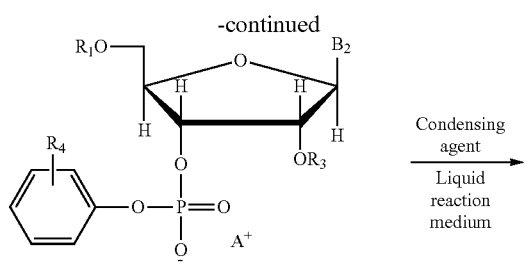

Formula (2)

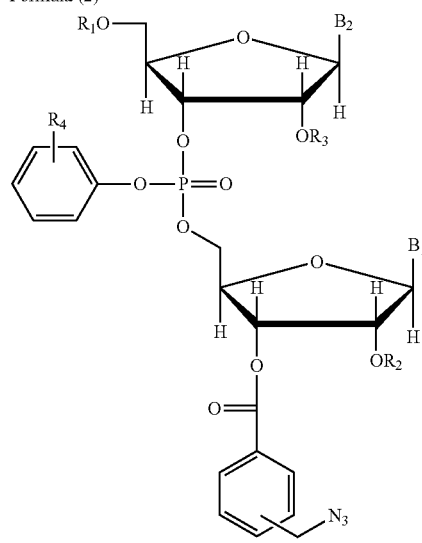

Formula (3)

The condition of the condensation reaction may comprise: 1-(2-mesitylenesulfonyl)-3-nitro-1H-1,2,4-triazole (MSNT) may be applied as condensing agent. MSNT is represented by Formula (8):

Formula (8)

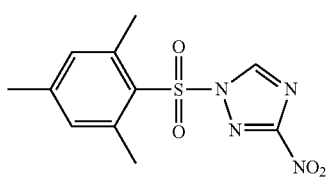

The reaction medium may be pyridine.

Relative to 1 mol of the compound represented by Formula (1), the amount of the compound represented by Formula (2) may be 0.8-3 mol, preferably 1-2 mol and more preferably 1-1.3 mol; the amount of the condensing agent may be 2-5 mol and preferably 2.5-3 mol; the amount of the reaction medium may be 5-50 L and preferably 5-20 L.

The reaction temperature of the reaction shown in Reaction Scheme I may be 10-50° C. and preferably 20-35° C.; the reaction time may be 0.5-10 h and preferably 1-5 h.

In Formulae (1), (2) and (3), the sterically hindered trisubstituted silyl protective group may be any kind of silane groups with the functions of steric hindrance and protection. The preferred may be tert-butyl dimethyl silyl, phenyl dimethyl silyl, tert-butyl diphenyl silyl or triisopropyl silyl. The more preferred may be tert-butyl dimethyl silyl.

The halogen atom may be F, Cl, Br or I. The preferred may be Cl or Br. The more preferred may be Cl.

The alkyl groups in the tri-alkyl ammonium ion may be same or different and may each have 1-6 carbon atoms, and preferably 1-4 carbon atoms. The particularly preferred alkyl groups include but are not limited to methyl, ethyl, n-propyl, iso-propyl, n-butyl, iso-butyl and tert-butyl.

The acyl in $B_1$ and $B_2$ may be acyl containing 2-10 carbon atoms. The preferred may be benzoyl, isobutyryl or acetyl.

In Formula (1) or (3), —$CH_2$—$N_3$ may be at ortho-, meta- or para-position, and preferably at ortho-position.

In Formula (2) or (3), $R_4$ may be in ortho-, meta- or para-position, and preferably at ortho-position.

After the reaction in Reaction Scheme I is completed, the reaction may be terminated and the product is separated.

The process for terminating the reaction may comprise: mixing the reaction solution with an aqueous solution of triethylammonium bicarbonate (TEAB) and holding for 10-90 min under stirring. The concentration of TEAB may be 0.1-1 mol/L. The ratio by volume of TEAB to the reaction medium may be 0.02-0.5.

The separation method may comprise: mixing the reaction solution with dichloromethane after the reaction is terminated, adding TEAB to wash it, and subjecting the organic phase to drying, filtering, concentrating and separating in a normal-pressure column to obtain the product. The ratio by volume of dichloromethane to the reaction medium may be 2-20. The concentration of TEAB may be 0.05-0.5 mol/L. The washing may be performed one or more times. The ratio between the total volume of TEAB for washing and the volume of the reaction medium may be 2-20. The drying, filtration, concentration and normal-pressure column separation methods are well-known to those skilled in the art and will not be detailedly described here.

If necessary, after the reaction in Reaction Scheme I is completed, the 5'-protective groups of the obtained DNA or RNA short chains may be removed (the second-step reaction shown in Reaction Scheme II), condensation reaction with the new compound represented by Formula (2) takes place again to obtain longer chains, the reaction is repeated several times and finally all protective groups are removed such that the oligonucleotides with the needed length are obtained; alternatively, the 3'-protective groups of the newly obtained DNA or RNA short chains may be removed, then 3'-hydroxyl phosphate is esterified to generate a new P-component (the reaction shown in Reaction Scheme III), it may again take condensation reaction with the new compound represented by Formula (3) to obtain longer chains, the reaction is repeated several times and finally all protective groups are removed such that the expected oligonucleotides are obtained. According to the method provided by the present invention, the compound represented by Formula (1) may be obtained from the reaction shown in Reaction Scheme II. That is, the compound represented by Formula (4) reacts with the compound represented by Formula (5) under the condensation reaction condition and then 5'-$R_5$ protective group is removed.

Reaction Scheme (II)

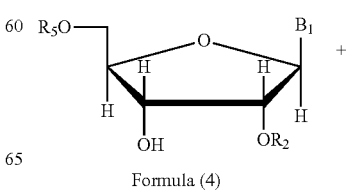

Formula (4)

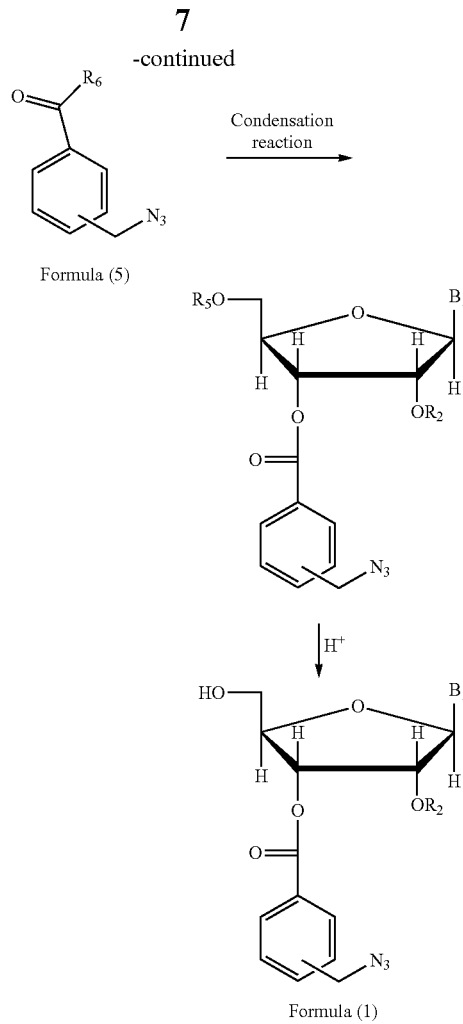

In Formula (4) and Formula (5), $R_2$ represents a sterically hindered trisubstituted silyl protective group. It may be any kind of silane group with the functions of steric hindrance and protection. The preferred one may be tert-butyl dimethyl silyl, phenyl dimethyl silyl, tert-butyl diphenyl silyl or triisopropyl silyl. The more preferred one may be tert-butyl dimethyl silyl.

$R_5$ represents DMTr.

$R_6$ represents a halogen atom. The halogen atom may be F, Cl, Br or I. The preferred one may be Cl or Br. The more preferred one may be Cl.

$B_1$ represents 9-guaninyl substituted with N-acyl, 9-adeninyl substituted with N-acyl, 1-cytosinyl substituted with N-acyl, 1-thyminyl or 1-uracilyl. The acyl may be acyl containing 2-10 carbon atoms. The preferred one may be benzoyl, isobutyryl or acetyl.

In Formula (1) or Formula (5), —$CH_2$—$N_3$ may be at ortho-, meta- or para-position, and preferably at ortho-position.

In Reaction Scheme II, the condensation reaction condition may comprise: using N-methylimidazole as an adjuvant; and using one or more of dichloromethane and pyridine as reaction medium.

Relative to 1 mol of the compound represented by Formula (4), the amount of the compound represented by Formula (5) may be 1-3 mol and preferably 1.5-3 mol; the amount of the adjuvant may be 1-8 mol and preferably 2-3.5 mol; the amount of the reaction medium may be 20-200 L and preferably 30-150 L.

The reaction temperature may be −10° C.~10° C. and the reaction is preferably performed in an ice bath; the reacion time may be 5-100 h and preferably 10-60 h.

After the condensation reaction in Reaction Scheme II is completed, the reaction may be terminated and the product of the condensation reaction is separated.

The reaction termination method may comprise: mixing the reaction solution with a saturated aqueous solution of $NaHCO_3$ for 1-20 min. The ratio by volume of the saturated aqueous solution of $NaHCO_3$ to the reaction medium may be 1-10.

The separation method may comprise: separating the organic phase and water phase of the reaction solution after the reaction is terminated, washing the organic phase with a saturated aqueous solution of $NaHCO_3$ and subjecting the organic phase to drying, filtering, concentrating and separating in a normal-pressure column to obtain the product. The washing may be performed one or more times. The ratio between the total volume of the saturated aqueous solution of $NaHCO_3$ and the volume of the reaction medium may be 1-20. The drying, filtration, concentration and normal-pressure column separation methods are well-known to those skilled in the art and will be not detailedly described here.

The method to remove 5'-$R_5$ protective group may comprise: the product of the condensation reaction reacts with formic acid in chloroform under stirring at 10-50° C. for 5-60 min. After the reaction, the organic phase and the formic acid phase may be directly separated, the formic acid phase is extracted with dichloromethane, and all organic phase is dried, filtered, concentrated, and separated in a normal-pressure column to obtain the product. The extraction may be performed one or more times. The ratio between the total volume of dichloromethane used during extraction and the volume of formic acid may be 1-20. The drying, filtration, concentration and normal-pressure column separation methods are well-known to those skilled in the art and will not be detailedly described here. Relative to 1 mol of the product of the condensation reaction, the amount of formic acid may be 10-50 L.

The method to remove 5'-$R_5$ protective group may also comprise: stirring the condensation product in 1% p-toluene sulfonic acid or 3%-5% trichloroacetic acid or 3%-5% trifluoroacetic acid in dichloromethane 1-60 min. The number of equivalents of the contained organic acids is 5-20 times of the reaction stoichiometric number. After the reaction is completed, the solution is neutralized with a saturated aqueous solution of $NaHCO_3$ and the organic phase is separated. The product is obtained after the organic phase is dried, filtered, concentrated, and separated in a normal-pressure column. The drying, filtration, concentration and normal-pressure column separation methods are well-known to those skilled in the art and will not be detailedly described here.

The method to remove 3'-protective group may comprise: the condensation product reacts with triphenylphosphine or diphenyl methyl phosphine in dioxane containing 10% water under stirring at 10-50° C. overnight. After the reaction is completed, the solvent will be evaporated. The product may be obtained through separation in a normal-pressure column. Relative to 1 mol of the product of the condensation reaction, the amount of triphenylphosphine or diphenyl methyl phosphine may be 3-5 mol and the amount of dioxane may be 50-150 L. The distillation and normal-pressure column separation methods are well-known to those skilled in the art and will not be detailedly described here.

The preparation method of the compound represented by Formula (5) may comprise the following steps:

(1) in the presence of benzoyl peroxide, the compound represented by Formula (9) reacts with N-halogenated succinimide to obtain the compound represented by Formula (10);

(2) the compound represented by Formula (10) reacts with alkali metal azide to obtain the compound represented by Formula (11);

(3) the compound represented by Formula (11) is hydrolyzed and acylated to obtain the compound represented by Formula (5),

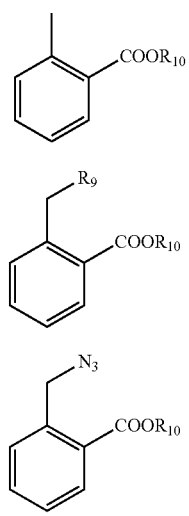

Formula (9)

Formula (10)

Formula (11)

where: $R_9$ represents a halogen atom; $R_{10}$ represents $C_1$-$C_4$ alkyl.

In step (1), the reaction medium may be one or more of carbon tetrachloride, chloroform, benzene, toluene and heptane. Relative to 1 mol of the compound represented by Formula (9), the amount of N-halogenated succinimide may be 1-3 mol and preferably 1-1.2 mol; the amount of benzoyl peroxide may be 0.01-0.1 mol and preferably 0.1-0.2 mol; the amount of the reaction medium may be 5-20 L and preferably 6-10 L; the reaction temperature may be 80~120° C. and preferably 90° C.~110° C.; and the reaction time may be 0.5-6 h and preferably 1-3 h.

In step (2), the reaction medium may be one or more of ethanol, acetone, N,N-dimethyl formamide and dimethyl sulfoxide. Relative to 1 mol of the compound represented by Formula (10), the amount of alkali metal azide may be 1-3 mol and preferably 1.5-2 mol; the amount of the reaction medium may be 3-10 L and preferably 6-8 L; the reaction temperature may be 0° C.~80° C., and preferably 25° C.~35° C.; and reaction time may be 2-30 h.

In step (3), the hydrolysis comprises the reaction between the compound represented by Formula (11) and the alcohol-water mixed solution (volume ratio 1:1) of alkali metal hydroxide. Relative to 1 mol of the compound represented by Formula (10), the amount of alkali metal hydroxide may be 5-100 mol and preferably 10-20 mol; the reaction temperature may be 0° C.~50° C. and preferably 25° C.~35° C.; the reaction time may be 0.1-2 h and preferably 0.25-1 h; and the concentration of alkali metal hydroxide in the alcohol-water mixed solution may be 5-10 wt %.

The compound represented by Formula (2) may be obtained from the reaction shown in Reaction Scheme III, i.e.: the reaction of the compound represented by Formula (6), the compound represented by Formula (7) and trialkyl amine in a reaction medium in the presence of a catalyst, Reaction Scheme III

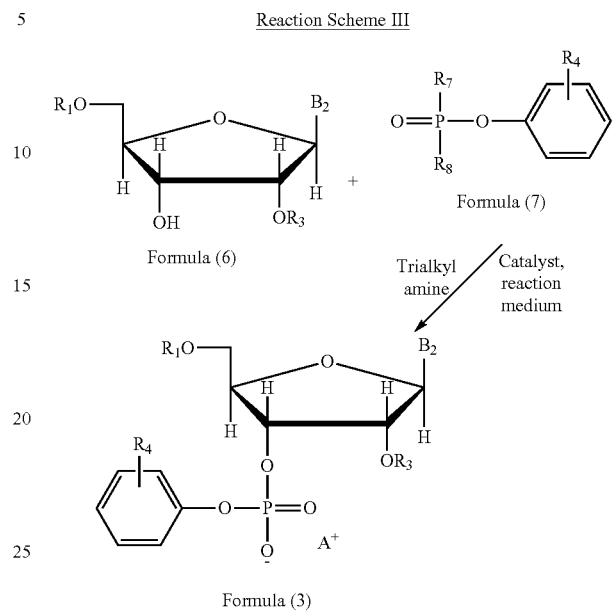

Formula (6)

Formula (7)

Formula (3)

The catalyst may be one or more of 1,2,4-triazole, triethylamine and pyridine.

The reaction medium may be one or more of dichloromethane, dioxane and tetrahydrofuran.

In Formula (6) and Formula (7), $R_1$ represents DMTr, or a covalently attached 5'-substituent derived from RNA or from DNA;

$R_3$ represents a sterically hindered trisubstituted silyl protective group and may be any kind of silane group with the functions of steric hindrance and protection, in which the preferred one may be tert-butyl dimethyl silyl, phenyl dimethyl silyl, tert-butyl diphenyl silyl or triisopropyl silyl and the more preferred one may be tert-butyl dimethyl silyl.

$R_4$, $R_7$ and $R_8$ each independently represent a alogen atom. The halogen atoms may be F, Cl, Br or I. The preferred may be Cl or Br. The more preferred may be Cl.

$B_2$ represents 9-guaninyl substituted with N-acyl, 9-adeninyl substituted with N-acyl, 1-cytosinyl substituted with N-acyl, 1-thyminyl or 1-uracilyl. The acyl may be an acyl containing 2-10 carbon atoms. The preferred one may be benzoyl, isobutyryl or acetyl.

In Formula (3) or Formula (7), $R_4$ may be at ortho-, meta- or para-position, and preferably at ortho-position.

The condition of the reaction shown in Reaction Scheme III may comprise: the reaction temperature may be −10 ~10 and the reaction is preferably performed in an ice bath; the reaction may be divided into two steps, the reaction time in the first step may be 0.5-10 h and preferably 1-3 h.

Relative to 1 mol of the compound represented by Formula (6), the amount of the compound represented by Formula (7) may be 1-5 mol and preferably 1.5-3 mol; the amount of trialkyl amine may be 1-50 mol and preferably 3-20 mol; the amount of catalyst may be 2-10 mol and preferably 2-6 mol; the amount of the reaction medium may be 5-200 L and preferably 10-100 L.

After the reaction in the first step is completed, the reaction solution and TEAB are mixed and held for 10-90 min under stirring. The concentration of TEAB may be 0.1-1 mol/L and the ratio by volume of TEAB to the reaction medium may be 0.2-2; then the organic phase and water phase are directly separated, the organic phase is washed with TEAB and the product may be obtained through drying, filtering, concentrating and separating in a normal-pressure column the organic phase. The concentration of the TEAB for washing may be 0.1-1 mol/L. The washing may be performed one or more times. The ratio by volume of the TEAB for washing to the reaction medium may be 0.5-5.

Hereinafter the present invention will be further described with reference to the examples.

The raw materials used in the examples are as follows:
Nucleotide 1 (A): The compound represented by Formula (6), protected adenine ribonucleotid, in which $B_2$ is N-benzoyl adenine, $R_1$ is DMTr and $R_3$ is tert-butyl dimethyl silyl. It is purchased from Shanghai GenePharma Co., Ltd.;
Nucleotide 2 (A): The compound represented by Formula (4), protected adenine ribonucleotide, in which $B_1$ is N-benzoyl adenine, $R_5$ is DMTr and $R_2$ is tert-butyl dimethyl silyl. It is purchased from Shanghai GenePharma Co., Ltd.;
Nucleotide 3 (C): The compound represented by Formula (6), protected cytosine ribonucleotide, in which $B_2$ is N-benzoyl cytosine, $R_1$ is DMTr and $R_3$ is tert-butyl dimethyl silyl. It is purchased from Shanghai GenePharma Co., Ltd.;
Nucleotide 4 (G): The compound represented by Formula (4), protected guanine ribonucleotide, in which $B_1$ is N-acetyl guanine, $R_5$ is DMTr and $R_2$ is tert-butyl dimethyl silyl. It is purchased from Shanghai GenePharma Co., Ltd.;
Nucleotide 5 (G): The compound represented by Formula (6), protected guanine ribonucleotide, in which $B_2$ is N-benzoyl guanine, $R_1$ is DMTr and $R_3$ is tert-butyl dimethyl silyl. It is purchased from Shanghai GenePharma Co., Ltd.;
Nucleotide 6 (U): The compound represented by Formula (4), protected uracil ribonucleotide, in which $B_1$ is uracil, $R_5$ is DMTr and $R_2$ is tert-butyl dimethyl silyl. It is purchased from Shanghai GenePharma Co., Ltd.;
Nucleotide 7 (U): The compound represented by Formula (6), protected uracil ribonucleotide, in which $B_2$ is uracil, $R_1$ is DMTr and $R_3$ is tert-butyl dimethyl silyl. It is purchased from Shanghai GenePharma Co., Ltd.;
Triethylamine: Purchased from Tianjin Beifang Tianyi Chemical Reagents Factory; 1,2,4-triazole: Purchased from Alfa Aesar;
2-chlorophenyl dichlorophosphate: The compound represented by Formula (7), in which $R_4$, $R_7$ and $R_8$ are all $C_1$ and $R_4$ is at ortho-position. It is purchased from Alfa Aesar;
o-azido methyl benzoyl chloride: The compound represented by Formula (5), in which $R_6$ is Cl and at ortho-position. It is obtained in the synthesis example 6.

MSNT: The compound represented by Formula (8), purchased from Sigma Aldrich.

Synthesis Example 1

This synthesis example is intended to prepare the raw material of the compound represented by Formula (3), i.e.: the compound (P-component) represented by Formula (2).

Add 1,2,4-triazole (2.76 g, 40 mmol) and triethylamine (10.1 g, 100 mmol) into a 250 ml round bottom flask, dissolve them in 15 ml of dichloromethane, dropwise add 10 ml of dichloromethane solution containing 2-chlorophenyl dichlorophosphate (4.91 g, 20 mmol) in ice bath, then dropwise add 35 ml of dichloromethane solution containing nucleotide 1 (7.87 g, 10 mmol), stir for 2.5 h in ice bath, then add 35 ml of 1M TEAB, continue to stir for 0.5 h, then add 1M TEAB to extract it three times (20 ml each time), dry all organic phase over anhydrous sodium sulfate, filter it and remove the solvent through rotary evaporation to obtain 10.78 g of the product with a yield of 100%. $^{31}$PNMR (CDCl$_3$, 121M) δ-6.09. ESI-MS, M$^-$ 976.2926. The yield is the percentage between the weight of the product and the calculated theoretical output of nucleotide 1.

Synthesis Example 2

This synthesis example is intended to prepare the raw material of the compound represented by Formula (3), i.e.: the compound (OH-component) represented by Formula (1).

Add N-methyl imidazole (2.08 g, 25 mmol) into a 250 ml round bottom flask, dissolve it in 15 ml of dichloromethane, dropwise add 15 ml of dichloromethane solution containing o-azido methyl benzoyl chloride (4.18 g, 20 mmol) in ice bath, then dropwise add 40 ml of dichloromethane solution containing nucleotide 2 (7.87 g, 10 mmol), continue to react in ice bath for 40 h and add 100 ml of saturated NaHCO$_3$ to terminate the reaction. After liquid separation, the organic phase is washed two times with saturated NaHCO$_3$ (100 ml each time), dried over anhydrous sodium sulfate, filtered, concentrated and separated in a normal-pressure column to obtain 8.21 g of the product with a yield of 86.8%. The yield is the percentage between the weight of the product and the calculated theoretical output of nucleotide 2.

Add and dissolve the product obtained above (8.21 g, 8.67 mmol) into 170 ml of chloroform, add 170 ml of HCOOH under quick stirring (stirring speed 500-1000 rpm), react at room temperature for 30 min, directly separate the solution, extract the HCOOH phase with dichloromethane three more times (170 ml of dichloromethane each time), combine the extraction liquid, wash it with water three times (170 ml of water each time), wash it with 0.1M TEAB one time (170 ml), dry the organic phase over anhydrous sodium sulfate and then filter, concentrate and separate in a normal-pressure column the organic phase to obtain 4.78 g of the product with a yield of 85.5%. The yield is the percentage between the weight of the product and the calculated theoretical output of nucleotide 2.

$^1$HNMR (CDCl$_3$, 300M) δ(−0.32, 3H, 1CH$_3$), (−0.00, 3H, 1CH$_3$), (−0.77, 9H, 3CH$_3$), 1.89 (s, 1H), 4.01-4.28 (dd, 2H, CH$_2$), 4.99 (s, 2H, CH$_2$), 5.42-5.46 (t, 1H), 5.88, 5.90 (d, 1H), 6.09, 6.12 (d, 1H), 6.26 (d, 1H), 7.37 (s, 1H), 7.58-7.79 (m, 5H), 8.16-8.31 (m, 4H), 8.98 (s, 1H), 9.22 (s, 1H), ESI-MS: (M+Na)$^+$667.2419

Synthesis Example 3

The synthesis is performed in the same manner as the synthesis example 1, except that nucleotide 1 is substituted with nucleotide 3.

Synthesis Example 4

The synthesis is performed in the same manner as the synthesis example 2, except that nucleotide 2 is substituted with nucleotide 4.

Synthesis Example 5

The synthesis is performed in the same manner as the synthesis example 1, except that nucleotide 1 is substituted with nucleotide 5.

Synthesis Example 6

The synthesis is performed in the same manner as the synthesis example 1, except that nucleotide 1 is substituted with nucleotide 7.

Synthesis Example 7

The synthesis is performed in the same manner as the synthesis example 2, except that nucleotide 2 is substituted with nucleotide 6.

Synthesis Example 8

The synthesis is performed in the same manner as the synthesis example 2, except that nucleotide 2 is substituted with nucleotide 3.

Synthesis Example 9

This synthesis example synthesizes the compound represented by Formula (5).

(1) Add 10.0 g of compound 1 into a 250 ml round bottom flask provided with a reflux device, add 80 ml of SOCl$_2$, heat and reflux the solution and react under stirring at 90 for 5 h. Change the reflux device into a distiller and distill out solvent SOCl$_2$. Add 60 ml of methanol after cooling, dropwise add 15 ml of triethylamine at room temperature under stirring and continue the reaction at room temperature for 30 min under stirring. Convert all acyl chloride into ester, remove excessive methanol and triethylamine through rotary evaporation, add 50 ml of ethyl acetate, wash it with water twice and with saturated NaCl water solution once and then dry the ester layer over anhydrous Na$_2$SO$_4$. After the solvent is removed, 9.7 g of compound 2 is obtained with a yield of 88.2%.

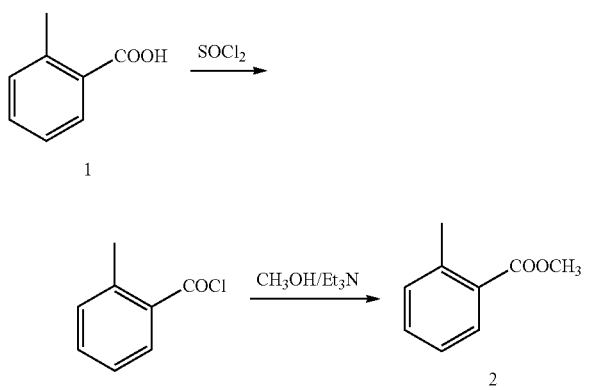

(2) Add 1.50 g (10 mmol) of compound 2 into a 250 ml round bottom flask, dissolve it in 80 ml of CCl$_4$, then add 1.98 g (11 mmol) of NBS and 48 mg (0.2 mmol) of BPO and heat and reflux for 1.5 h to complete reaction. Remove the floating insolubles through filtration and then remove the solvent to obtain compound 3. The reaction is quantitative.

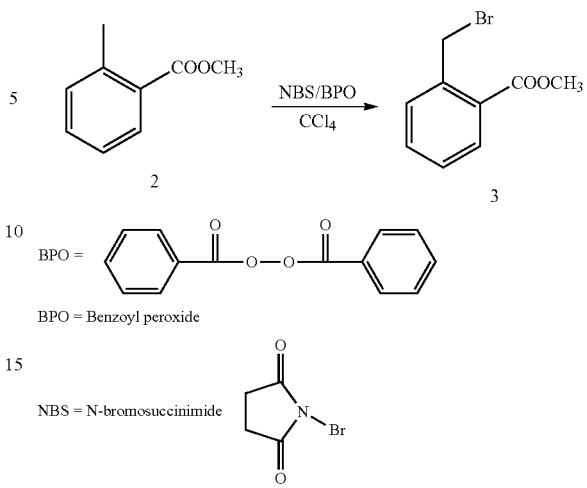

(3) Add 916 mg (4 mmol) of compound 3 into a 250 ml round bottom flask, dissolve it in 20 ml of ethanol, then add 520 mg (8 mmol) of NaN$_3$ and stir at room temperature overnight (21 h). Remove ethanol through rotary evaporation, add ethyl acetate to dissolve it, wash it with water and saturated NaCl water solution in turn, remove solvent from the organic layer through rotary evaporation, add 40 ml of 5% NaOH solution (CH$_3$OH:H$_2$O=1:1 v/v), stir at room temperature for 30 min, remove methanol through rotary evaporation, regulate pH to about 1 with 2.5M HCl and extract with CH$_2$Cl$_2$ 4 times. Dry the organic phase over anhydrous Na$_2$SO$_4$ and remove solvent to obtain compound 5. Re-crystallize compound 5 with cyclohexane to obtain white crystal.

NMR data of compound 5:

$^1$HNMR (CDCl$_3$, 400M), 4.89, (s, 2H, CH$_2$), 7.43-7.47 (t, 1H), 7.54-7.56 (d, 1H), 7.61-7.64 (t, 1H), 8.18-8.20 (d, 1H).

Element analysis: C, 53.80; H, 3.99; N, 23.92, calculated value: C, 54.24; H, 3.98, N, 23.72

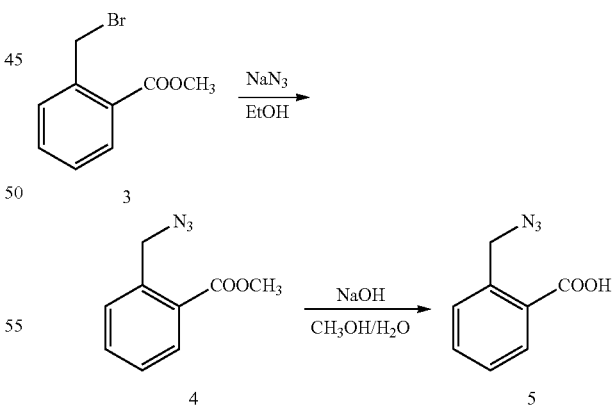

(4) Add 1.0 g (5.65 mmol) of compound 5 into a 100 ml round bottom flask, dissolve it in 50 ml of CHCl$_3$, then add 2.02 g (16.95 mmol) of SOCl$_2$ and heat and reflux for 5 h. Remove the solvent through rotary evaporation after the reaction is stopped, bring out excessive SOCl$_2$ through azetropy of toluene 3×3 ml to obtain compound 6, and store it in a desiccator for future use.

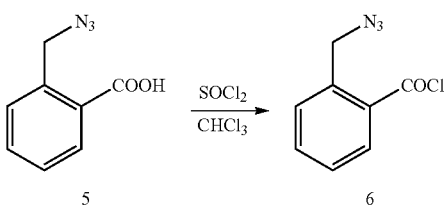

Example 1

This example synthesizes oligonucleotides.
Synthesis Target: Fully Protected RNA
DMTr [CGAAAGAACG] AZMB (SEQ ID NO. 1)
Note: [ ] indicates fully protected RNA except 3' and 5' ends
DMTr is 4,4'-dimethoxytriphenylmethyl, a protective group at 5' end;
AZMB is o-azido methyl benzoyl chloride, a protective group at 3' end.

(1) Synthesis of DMTr [CpG] AZMB

Add the product of synthesis example 4 (598 mg, 1 mmol) and the product of synthesis example 3 (1.19 g, 1.2 mmol) into a 25 ml round bottom flask, add 10 ml of anhydrous pyridine to dissolve the sample, add MSNT by three times (745 mg, 2.8 mmol in total) and stir at room temperature for 3 h. Add 1 ml of 1M TEAB, stir for 0.5 h to terminate the reaction, pour the reaction solution into 60 ml of dichloromethane, wash it with 0.1M TEAB three times (20 ml each time), dry the organic phase over anhydrous sulfate and filter, concentrate and separate in a normal-pressure column to obtain 831 mg of the product with a yield of 56.4%. The yield is the percentage between the weight of the product and the calculated theoretical output calculated according to the product of synthesis example 4.

(2) Synthesis of OH-[CpG]AZMB

Dissolve DMTr[CG]AZMB (800 mg, 0.54 mmol) obtained in step (1) in 7.5 ml of chloroform, add 7.5 ml of HCOOH under quick stirring, react at room temperature for 30 min, directly separate the solution, extract the HCOOH phase with dichloromethane three times (5 mL each time), combine the extraction liquid, wash it with water three times (5 ml each time) and with 0.1M TEAB (10 ml) once. Dry the organic phase over anhydrous sodium sulfate and then filter, concentrate and separate in a normal-pressure column the organic phase to obtain 500 mg of the product with a yield of 79.1%. The yield is the percentage between the weight of the product and the calculated theoretical output of DMTr[CG]AZMB.

(3) Synthesis of DMTr[AA]AZMB

Add the product of synthesis example 2 (1.39 g, 2.16 mmol) and the product of synthesis example 1 (3.03 g, 2.81 mmol) into a 100 ml round bottom flask, add 22 ml of anhydrous pyridine to dissolve the sample, add MSNT (1.80 g, 6.05 mmol) by three times and stir at room temperature for 2 h. Add 1M TEAB, stir for 0.5 h to terminate the reaction, pour the reaction solution into 150 ml of dichloromethane, wash it with 0.1M TEAB three times, dry the organic phase over anhydrous sodium sulfate and filter, concentrate and separate in a normal-pressure column to obtain 3.08 g of the product with a yield of 87.9%. The yield is the percentage between the weight of the product and the calculated theoretical output calculated according to the product of synthesis example 2.

(4) Synthesis of OH[AA]AZMB

Dissolve DMTr[AA]AZMB (3.08 g, 1.92 mmol) obtained in step (3) in 100 ml of 1% p-toluene sulfonic acid solution, stir at room temperature for 30 min, separate the organic phase after neutralization with saturated NaHCO$_3$, extract the water phase with dichloromethane twice, combine the organic phase, dry the organic phase over anhydrous sodium sulfate and then filter, concentrate and separate in a normal-pressure column the organic phase to obtain 2.45 g of the product with a yield of 98.8%. The yield is the percentage between the weight of the product and the calculated theoretical output calculated according to DMTr[AA]AZMB.

(5) Synthesis of DMTr[GAA]AZMB

Add OH[AA]AZMB (2.45 g, 1.88 mmol) obtained in step (4) and the product of synthesis example 5 (2.39 g, 2.26 mmol) into a 100 ml round bottom flask, add 19 ml of anhydrous pyridine to dissolve the sample, add MSNT (1.56 g, 5.26 mmol) by three times and stir at room temperature for 2 h. Add 2 ml of 1M TEAB, stir for 0.5 h to terminate the reaction, pour the reaction solution into 200 ml of dichloromethane, wash it with 0.1M TEAB three times, dry the organic phase over anhydrous sodium sulfate and filter, concentrate and separate in a normal-pressure column the organic phase to obtain 4.068 g of the product with a yield of 96.0%. The yield is the percentage between the weight of the product and the calculated theoretical output calculated according to OH[AA]AZMB.

(6) Synthesis of OH[GAA]AZMB

Dissolve DMTr[GAA]AZMB (4.068 g, 1.8 μmol) obtained in step (5) in 50 ml of chloroform, add 50 ml of HCOOH under quick stirring, react at room temperature for 30 min, directly separate the solution, extract the HCOOH phase with dichloromethane three times, combine the extraction liquid, wash it with water three times and with 0.1M TEAB once, dry the organic phase over anhydrous sodium sulfate and filter, concentrate and separate in a normal-pressure column to obtain 2.66 g of the product with a yield of 75.6%. The yield is the percentage between the weight of the product and the calculated theoretical output calculated according to DMTr[GAA]AZMB.

(7) Synthesis of DMTr[AGAA]AZMB

Add OH[GAA]AZMB (1.48 g, 0.76 mmol) obtained in step (6) and the product of synthesis example 1 (1.08 g, 1.00 mmol) into a 100 ml round bottom flask, add 8 ml of anhydrous pyridine to dissolve the sample, add MSNT (632 mg, 2.13 mmol) by three times and stir it at room temperature for 4 h. Add 1.5 ml of 1M TEAB, stir for 0.5 h to terminate the reaction, pour the reaction solution into 60 ml of dichloromethane, wash it with 0.1M TEAB three times, dry the organic phase over anhydrous sodium sulfate and filter, concentrate and separate in a normal-pressure column the organic phase to obtain 2.21 g of crude product.

(8) Synthesis of DMTr[AGAA]OH

Add DMTr[AGAA]AZMB (2.21 g, 0.76 mmol) obtained in step (7) into a 100 ml round bottom flask, add 2.6 g mixed solvent of dioxane/water (9:1) to dissolve it, add triphenylphosphine (796 mg, 3.04 mmol), stir at room temperature for 24 h, evaporate the solvent and separate in a normal-pressure column to obtain 2.1 g of crude product.

(9) Synthesis of DMTr[AGAA]PO$^-$

Add 1,2,4-triazole (420 mg, 6.08 mmol) and triethylamine (768 mg, 7.60 mmol) into a 100 ml round bottom flask, dissolve them in 7 ml of dichloromethane, dropwise add 3 ml of dichloromethane solution containing 2-chlorophenyl dichlorophosphate (560 mg, 2.28 mmol) in ice bath, then dropwise add 2.5 ml of dichloromethane solution containing DMTr[AGAA]OH (2.1 g, 0.76 mmol) obtained in step (8), stir in ice salt bath for 2.5 h, add 3 ml of TEAB to terminate the reaction, wash it with 0.1M TEAB three times, dry the organic phase over anhydrous sodium sulfate and filter, concentrate and separate in a normal-pressure column the organic phase to obtain 1.31 g of the product with 56.7% of total yield in the three steps.

(10) Synthesis of DMTr[CGAA]AZMB

Add OH[GAA]AZMB (1.12 g, 0.58 mmol) obtained in step (6) and the product of synthesis example 3 (746 mg, 0.75 mmol) into a 100 ml round bottom flask, add 6 ml of anhydrous pyridine to dissolve the sample, add MSNT (482 mg, 1.62 mmol) by three times and stir at room temperature for 4 h. Add 1.5 ml of 1M TEAB, stir for 0.5 h to terminate the reaction, pour the reaction solution into 60 ml of dichloromethane, wash it with 0.1M TEAB three times, dry the organic phase over anhydrous sodium sulfate and filter, concentrate and separate in a normal-pressure column the organic phase to obtain 1.63 g of crude product.

(11) Synthesis of DMTr[CGAA]OH

Add DMTr[CGAA]AZMB (1.60 g, 0.57 mmol) obtained in step (10) into a 100 ml round bottom flask, dissolve it in 1.6 g mixed solvent of dioxane/water (9:1), add triphenylphosphine (595 mg, 2.27 mmol), stir at room temperature for 24 h, evaporate the solvent and separate in a normal-pressure column to obtain 1.5 g of crude product.

(12) Synthesis of DMTr[CGAA]PO$^-$

Add 1,2,4-triazole (315 mg, 4.56 mmol) and triethylamine (576 mg, 5.70 mmol) into a 25 ml round bottom flask, dissolve them in 5 ml of dichloromethane, dropwise add 2 ml of dichloromethane solution containing 2-chlorophenyl dichlorophosphate (420 mg, 1.71 mmol) in ice bath, then dropwise add 2 ml of dichloromethane solution containing DMTr[CGAA]OH (1.5 g, 0.57 mmol) obtained in step (11), stir in ice salt bath for 2.5 h, add 1.5 ml of TEAB to terminate the reaction, wash it with 0.1M TEAB three times, dry the organic phase over anhydrous sodium sulfate and filter, concentrate and separate in a normal-pressure column the organic phase to obtain 1.12 g of the product with 61.9% of total yield in the three steps.

(13) Synthesis of DMTr[AGAACG]AZMB

Add OH[CG]AZMB (480 mg, 0.41 mmol) obtained in step (2) and DMTr[AGAA]PO$^-$ (1.20 g, 0.40 mmol) obtained in step (9) into a 25 ml round bottom flask, add 8 ml of anhydrous pyridine to dissolve the sample, add MSNT (333 mg, 1.12 mmol) by three times and stir it at room temperature for 2.5 h. Add 1 ml of 1M TEAB, stir for 0.5 h to terminate the reaction, pour the reaction solution into 60 ml of dichloromethane, wash it with 0.1M TEAB three times, dry the organic phase over anhydrous sodium sulfate and filter, concentrate and separate in a normal-pressure column the organic phase to obtain 1.21 g of the product with a yield of 73.4%.

(14) Synthesis of OH[AGAACG]AZMB

Add DMTr[AGAACG]AZMB (1.21 g, 0.29 mmol) obtained in step (13), add 10 ml of chloroform to dissolve it, add 10 ml of HCOOH under quick stirring, react at room temperature for 30 min, directly separate the solution, extract the HCOOH phase with dichloromethane three times, combine the extraction liquid, wash it with water three times and with 0.1M TEAB one time, dry the organic phase over anhydrous sodium sulfate and filter, concentrate and separate in a normal-pressure column the organic phase to obtain 863 mg of the product with a yield of 78.6%.

(15) Synthesis of DMTr[CGAAAGAACG]AZMB (SEQ ID NO. 1)

Add OH[AGAACG]AZMB (840 mg, 0.22 mmol) obtained in step (14) and DMTr[CGAA]PO$^-$ (786 g, 0.26 mmol) obtained in step (12) into a 25 ml round bottom flask, add 5 ml of anhydrous pyridine to dissolve the sample, add MSNT (184 mg, 0.62 mmol) by three times and stir at room temperature for 4 h. Add 1 ml of 1M TEAB, stir for 0.5 h to terminate the reaction, pour the reaction solution into 60 ml of dichloromethane, wash it with 0.1M TEAB three times, dry the organic phase over anhydrous sodium sulfate and filter, concentrate and separate in a normal-pressure column the organic phase to obtain 1.20 g of the product with a yield of 82.4%. MAIDI-TOF MS: 6560.787.

Example 2

This example synthesizes oligonucleotides.

```
Synthesis target:
                                        (SEQ ID NO. 1)
    5'-CGAAAGAACG-3'
```

(1) Dissolve 46 mg (0.28 mmol) of 4-nitrobenzaldoxime and 32 mg (0.28 mmol) of tetra methyl guanidine in 0.6 ml mixed solution of dioxane/water (v/v 1:1), mix them well, add 13 mg (2 umol) of DMTr[CGAAAGAACG]AZMB (SEQ ID NO. 1) obtained in example 1 and react at room temperature for 30 h. This step is to remove the protective group on phosphine.

(2) Centrifuge and dry at 40° C. under vacuum the reaction solution obtained in step (1), add 5 ml of concentrated ammonia (25%-28%), heat it to 50 and react 12 h. This step is to remove protective group on base and 3'-end.

(3) Centrifuge and dry at 40° C. under vacuum the reaction solution obtained in step (2), add 1 ml of 80% acetic acid, react at room temperature 30 min, centrifuge and dry again, dissolve the residue in 2 ml of water, wash it with 2 ml of ethyl acetate, and freeze and dry it at −80 under vacuum into dry powder. This step is to remove 5'-protective group.

(4) Add 1 ml of 1M TBAF tetrahydrofuran solution into the freeze-dry powder and react at 37 overnight. This step is to remove 2'-protective group. Add an equal volume of water into the fully reacted reaction solution to quench it, centrifuge and dry it at 40 under vacuum to remove tetrahydrofuran, desalt the residue in sephadex G25 column, and collect the product that has ultraviolet absorption at 260 nm to obtain aqueous solution of the deprotected oligo-RNA 5'-CGAAAGAACG-3' (SEQ ID NO. 1). Freeze dry it at −80 under vacuum into white dry powdery solid. MAIDI-TOF MS: 3233.67.

Example 3

This example synthesizes oligonucleotides.

```
Synthesis target: Fully protected RNA
                                        (SEQ ID NO. 2)
DMTr[UGCGCGUUGAUGUGAGGUUCCUU]AZMB
And
                                        (SEQ ID NO. 3)
DMTr[GGAACCUCACAUCAACGCGCAUU]AZMB
```

(1) Synthesis of OH[CG]AZMB

Add the product of synthesis example 3 (4.433 g, 4.2 mmol) and the product of synthesis example 4 (2.194 g, 3.5 mmol) into a 50 ml round bottom flask, add 30 ml of anhydrous pyridine to dissolve the sample, add MSNT (2.911 g, 9.8 mmol) and stir at room temperature for 2 h. Add 4 ml of 0.1M TEAB, stir for 10 min to terminate the reaction, remove the solvent through rotary evaporation, dissove the obtained product in 50 ml of $CH_2Cl_2$, wash it with 0.1M TEAB 3 times (20 ml each time), regulate pH value to 3 with 5% oxalic acid, separate the solution to obtain organic phase, dry the organic phase over anhydrous $Na_2SO_4$ and filter it to obtain 50 ml of filtrate. Transfer the obtained filtrate into a 250 ml round bottom flask, slowly add 50 ml of 6% $CF_3COOH$, stir and react at room temperature for 5 min, add saturated $NaHCO_3$ to neutralize the solution, separate the solution to obtain organic phase, wash the obtained organic phase with 20 ml of saturated $NaHCO_3$ once, dry the organic phase over anhydrous sodium sulfate and filter, concentrate and separate in a normal-pressure column the organic phase to obtain the product with a yield of 78%. The yield is the percentage between the weight of the product and the calculated theoretical output calculated according to the product of synthesis example 4.

(2) Synthesis of OH[GG]AZMB

The step same as step (1) is adopted to synthesize OH[GG]AZMB, except that the product of synthesis example 5 (4.471 g, 4.2 mmol) and the product of synthesis example 4 (2.194 g, 3.5 mmol) are adopted and dissolved in 20 ml of anhydrous pyridine and the amount of 0.1M TEAB is 3 ml. The yield is 67.1%. The yield is the percentage between the weight of the product and the calculated theoretical output calculated according to the product of synthesis example 4.

(3) Synthesis of OH[AU]AZMB

Add the product of synthesis example 1 (4.534 g, 4.2 mmol) and the product of synthesis example 7 (1.811 g, 3.5 mmol) into a 50 ml round bottom flask, add 20 ml of pyridine to dissolve the sample, add MSNT (2.911 g, 9.8 mmol) by batch and stir and react at room temperature for 2 h. Add 10 ml of 1M TEAB, stir for 10 min to terminate the reaction, dissolve it in 100 ml of $CH_2Cl_2$, wash it with 1M TEAB 3 times (20 ml each time), separate the solution to obtain organic phase, dry the organic phase over anhydrous $Na_2SO_4$ and filter, concentrate and separate in a normal-pressure column the organic phase to obtain the product. Dissolve the obtained product in 45 ml of $CH_2Cl_2$, slowly add 45 ml of 6% $CF_3COOH$ under stirring, ensure the concentration of $CF_3COOH$ in the system is 3%, and stir and react at room temperature for 5 min. Add saturated $NaHCO_3$ to neutralize the solution, separate the solution to obtain organic phase, wash the organic phase with 20 ml of saturated $NaHCO_3$ once, dry the organic phase over anhydrous sodium sulfate and filter, concentrate and separate in a normal-pressure column the organic phase to obtain the product with a yield of 81.1%. The yield is the percentage between the weight of the product and the calculated theoretical output calculated according to the product of synthesis example 7.

(4) Synthesis of OH[UU]AZMB

Add the product of synthesis example 6 (10.0 g, 10.5 mmol) and the product of synthesis example 7 (4.53 g, 8.75 mmol) into a 250 ml round bottom flask, add 45 ml of anhydrous pyridine to dissolve the sample, add MSNT (7.28 g, 24.5 mmol) by batch and stir and react at room temperature for 2 h. Add 50 ml of 1M TEAB, stir for 20 min to terminate the reaction, dissolve it in 300 ml of $CH_2Cl_2$, wash it with 1M TEAB 3 times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 100 ml of $CH_2Cl_2$, slowly add 100 ml of 6% $CF_3COOH$ under stirring and stir and react at room temperature for 5 min. Add saturated $NaHCO_3$ to neutralize the solution, separate the solution to obtain an organic phase, wash the organic phase with 50 ml of saturated $NaHCO_3$ once, dry the organic phase over anhydrous sodium sulfate and filter, concentrate and separate in a normal-pressure column the organic phase to obtain the product with a yield of 73%. The yield is the percentage between the weight of the product and the calculated theoretical output calculated according to the product of synthesis example 7.

(5) Synthesis of OH[CC]AZMB

Add the product of synthesis example 3 (31.66 g, 30 mmol) and the product of synthesis example 2 (16.12 g, 25 mmol) into a 500 ml round bottom flask, use 150 ml of anhydrous pyridine to dissolve the sample, add MSNT (20.79 g, 70 mmol) by batch and stir and react at room temperature 2 h. Add 100 ml of 1M TEAB, stir 20 min to terminate the reaction, dissolve it in 600 ml of $CH_2Cl_2$, wash it with 1M TEAB 3 times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 370 ml of $CH_2Cl_2$, slowly add 370 ml of 6% $CF_3COOH$ under stirring, ensure the concentration of $CF_3COOH$ in the system is 3%, and stir and react at room temperature for 5 min. Add saturated $NaHCO_3$ to neutralize the solution, separate the solution to obtain an organic phase, wash the organic phase with 20 ml of saturated $NaHCO_3$ once, dry the organic phase over anhydrous sodium sulfate and filter, concentrate and separate in a normal-pressure column the organic phase to obtain the product with a yield of 72%. The yield is the percentage between the weight of the product and the calculated theoretical output calculated according to the product of synthesis example 2.

(6) Synthesis of OH[CC]AZMB

A method same as step (4) is adopted to prepare OH[CC]AZMB, except that the product of synthesis example 3 (12.25 g, 11.6 mmol) and the product of synthesis example 8 (6.0 g, 9.67 mmol) are adopted, 50 ml of anhydrous pyridine is used to dissolve the sample and MSNT (8.01 g, 27.1 mmol) is added by batch. The yield is 83%. The yield is the percentage between the weight of the product and the calculated theoretical output calculated according to the product of synthesis example 8.

(7) Synthesis of OH[GC]AZMB

Add the product of synthesis example 5 (18.47 g, 17.4 mmol) and the product of synthesis example 8 (9.0 g, 14.5 mmol) into a 250 ml round bottom flask, use 72 ml of anhydrous pyridine to dissolve the sample, add MSNT (12.0 g, 40.6 mmol) by batch and stir and react at room temperature 2 h. Add 80 ml of 1M TEAB, stir 20 min to terminate the reaction, dissolve it in 300 ml of $CH_2Cl_2$, wash it with 1M TEAB 3 times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 150 ml of $CH_2Cl_2$, slowly add 150 ml of 6% $CF_3COOH$ under stirring, ensure the concentration of $CF_3COOH$ in the system is 3%, and stir and react at room temperature for 10 min. Add saturated $NaHCO_3$ to neutralize the solution, separate the solution to obtain an organic phase, wash the organic phase with 120 ml of saturated $NaHCO_3$ once and dry the organic phase over anhydrous $Na_2SO_4$. The yield is 63.8%. The yield is the percentage between the weight of the product and the calculated theoretical output calculated according to the product of synthesis example 8.

(8) Synthesis of OH[UG]AZMB

Add the product of synthesis example 6 (5.14 g, 5.4 mmol) and the product of synthesis example 4 (2.82 g, 4.5 mmol) into a 50 ml round bottom flask, use 30 ml of anhydrous pyridine to dissolve the sample, add MSNT (3.74 g, 12.6 mmol) by batch and stir and react at room temperature for 2 h. Add 10 ml of 1M TEAB, stir for 20 min to terminate the reaction, dissolve it in 150 ml of $CH_2Cl_2$, wash it with 1M TEAB 3 times (20 ml each time), separate the solution to obtain an organic phase, dry the organic phase over anhydrous Na$_2$SO$_4$ and filter, concentrate and separate in a normal-pressure column the organic phase to obtain the product. Dissolve the obtained product in 450 ml of CH$_2$Cl$_2$, slowly add 450 ml of 6% CF$_3$COOH under stirring, ensure the concentration of CF$_3$COOH in the system is 3%, and stir at room temperature 5 min. Add saturated NaHCO$_3$ to neutralize the solution, separate the solution to obtain an organic phase, wash the organic phase with 300 ml of saturated NaHCO$_3$ once, dry the organic phase over anhydrous sodium sulfate and filter, concentrate and separate in a normal-pressure column the organic phase to obtain the product with a yield of 78%. The yield is the percentage between the weight of the product and the calculated theoretical output calculated according to the product of synthesis example 4.

(9) Synthesis of DMTr[GG]AZMB

Add the product of synthesis example 5 (7.64 g, 7.2 mmol) and the product of synthesis example 4 (3.76 g, 6 mmol) into a 100 ml round bottom flask, add 35 ml of anhydrous pyridine to dissolve the sample, add MSNT (5.0 g, 16.8 mmol) by three times and stir at room temperature 2.5 h. Add 10 ml of 1M TEAB, stir 20 min to terminate the reaction, pour the reaction solution into 200 ml of CH$_2$Cl$_2$, wash it with 1M TEAB three times (20 ml each time), separate the solution to obtain an organic phase, dry the organic phase with Na$_2$SO$_4$ and filter, concentrate and separate in a normal-pressure column the organic phase to obtain the product with a yield of 81%. The yield is the percentage between the weight of the product and the calculated theoretical output calculated according to the product of synthesis example 4.

(10) Synthesis of DMTr[UGC]AZMB

Add the product of synthesis example 6 (7.67 g, 9.10 mmol) and OH[GC]AZMB (7.77 g, 6.17 mmol) obtained in step (7) into a 250 ml round bottom flask, add 40 ml of anhydrous pyridine to dissolve the sample, add MSNT (5.13 g, 17.3 mmol) by three times and stir it at room temperature for 3.5 h. Add 10 ml of 1M TEAB, stir for 20 min to terminate the reaction, pour the reaction solution into 150 ml of CH$_2$Cl$_2$, wash it with 1M TEAB three times (20 ml each time), dry the organic phase over Na$_2$SO$_4$ and filter, concentrate and separate in a normal-pressure column the organic phase to obtain the product with a yield of 73%. The yield is the percentage between the weight of the product and the calculated theoretical output calculated according to OH[GC]AZMB.

(11) Synthesis of DMTr[UCA]AZMB

Add the product of synthesis example 6 (8.67 g, 9.10 mmol) and OH[CA]AZMB (8.95 g, 7.00 mmol) obtained in step (5) into a 50 ml round bottom flask, add 50 ml of anhydrous pyridine to dissolve the sample, add MSNT (5.82 g, 19.6 mmol) by three times and stir at room temperature 4 h. Add 10 ml of 1M TEAB, stir 20 min to terminate the reaction, pour the reaction solution into 100 ml of CH$_2$Cl$_2$, wash it with 1M TEAB three times (20 ml each time), separate the solution to obtain an organic phase, dry the organic phase over Na$_2$SO$_4$ and filter, concentrate and separate in a normal-pressure column the organic phase to obtain the product with a yield of 77%. The yield is the percentage between the weight of the product and the calculated theoretical output calculated according to OH[CA]AZMB.

(12) Synthesis of DMTr[ACG]AZMB

A method same as step (11) is adopted to prepare DMTr[ACG]AZMB, except that the product of synthesis example 1 (2.67 g, 2.47 mmol) and OH[CG]AZMB (2.40 g, 1.90 mmol) obtained in step (1) are adopted, 15 ml of anhydrous pyridine is used to dissolve the sample and MSNT (1.58 g, 5.32 mmol) is added by three times. The yield is 78%. The yield is the percentage between the weight of the product and the calculated theoretical output calculated according to OH[CG]AZMB.

(13) Synthesis of DMTr[GUU]AZMB

Add the product of synthesis example 5 (4.30 g, 4.05 mmol) and OH[UU]AZMB (3.15 g, 3.00 mmol) obtained in step (4) into a 100 ml round bottom flask, use 20 ml of anhydrous pyridine to dissolve the sample, add MSNT (2.50 g, 8.40 mmol) by three times and stir at room temperature 2.5 h. Add 10 ml of 1M TEAB, stir 20 min to terminate the reaction, pour the reaction solution into 100 ml of CH$_2$Cl$_2$, wash it with 1M TEAB three times (30 ml each time), separate the solution to obtain an organic phase, dry the organic phase over Na$_2$SO$_4$ and filter, concentrate and separate in a normal-pressure column the organic phase to obtain the product with a yield of 79%. The yield is the percentage between the weight of the product and the calculated theoretical output calculated according to OH[UU]AZMB.

(14) Synthesis of DMTr[GUG]AZMB

Add the product of synthesis example 5 (4.29 g, 4.04 mmol) and OH[UG]AZMB (3.60 g, 3.11 mmol) obtained in step (8) into a 100 ml round bottom flask, use 20 ml of anhydrous pyridine to dissolve the sample, add MSNT (2.59 g, 8.71 mmol) by three times and stir it at room temperature 3.5 h. Add 10 ml of 1M TEAB, stir 20 min to terminate the reaction, pour the reaction solution into 100 ml of CH$_2$Cl$_2$, wash it with 1M TEAB three times (20 ml each time), separate the solution to obtain an organic phase, dry the organic phase over Na$_2$SO$_4$ and filter, concentrate and separate in a normal-pressure column the organic phase to obtain the product with a yield of 67% after purification by column chromatography. The yield is the percentage between the weight of the product and the calculated theoretical output calculated according to OH[UG]AZMB.

(15) Synthesis of OH[ACC]AZMB

Add the product of synthesis example 1 (5.62 g, 5.20 mmol) and OH[CC]AZMB (5.4 g, 4.33 mmol) obtained in step (6) into a 100 ml round bottom flask, use 22 ml of anhydrous pyridine to dissolve the sample, add MSNT (3.59 g, 12.1 mmol) by batch and stir and react at room temperature 3 h. Add 10 ml of 1M TEAB, stir 20 min to terminate the reaction, dissolve it in 150 ml of CH$_2$Cl$_2$, wash it with 1M TEAB 3 times (20 ml each time), separate the solution to obtain an organic phase, dry the organic phase over anhydrous Na$_2$SO$_4$ and filter, concentrate and separate in a normal-pressure column the organic phase to obtain the product. Dissolve the obtained product in 100 ml of CH$_2$Cl$_2$, slowly add 100 ml of 6% CF$_3$COOH under stirring, ensure the concentration of CF$_3$COOH in the system is 3%, and stir at room temperature for 30 min. Add saturated NaHCO$_3$ to neutralize the solution, separate the solution to obtain an organic phase, wash the organic phase with 80 ml of saturated NaHCO$_3$ once, dry the organic phase over anhydrous Na$_2$SO$_4$ and filter, concentrate and separate in a normal-pressure column the organic phase to obtain the product. The yield is 52%. The yield is the percentage between the weight of the product and the calculated theoretical output calculated according to OH[CC]AZMB.

(16) Synthesis of OH[GCA]AZMB

Add the product of synthesis example 5 (4.00 g, 3.77 mmol) and OH[CA]AZMB (4.2 g, 3.28 mmol) obtained in step (5) into a 100 ml round bottom flask, use 20 ml of anhydrous pyridine to dissolve the sample, add MSNT (2.73 g, 9.18 mmol) by batch and stir and react at room temperature for 3 h. Add 10 ml of 1M TEAB, stir 20 min to terminate the reaction, dissolve it in 150 ml of CH$_2$Cl$_2$, wash it with 1M TEAB 3 times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 35 ml of $CH_2Cl_2$, slowly add 35 ml of 6% $CF_3COOH$ under stirring, ensure the concentration of $CF_3COOH$ in the system is 3%, and stir at room temperature 30 min. Add saturated $NaHCO_3$ to neutralize the solution, separate the solution to obtain an organic phase, wash the organic phase with 25 ml of saturated $NaHCO_3$ once, dry the organic phase over anhydrous $Na_2SO_4$ and filter, concentrate and separate in a normal-pressure column the organic phase to obtain the product with a yield of 68%. The yield is the percentage between the weight of the product and the calculated theoretical output calculated according to OH[CA]AZMB.

(17) Synthesis of OH[UCC]AZMB

Add the product of synthesis example 6 (3.59 g, 3.77 mmol) and OH[CC]AZMB (2.42 g, 2.90 mmol) obtained in step (6) into a 50 ml round bottom flask, add 20 ml of anhydrous pyridine to dissolve the sample, add MSNT (2.41 g, 8.12 mmol) by batch and stir and react at room temperature for 5 h. Add 10 ml of 1M TEAB, stir for 20 min to terminate the reaction, dissolve it in 100 ml of $CH_2Cl_2$, wash it with 1M TEAB 3 times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 40 ml of $CH_2Cl_2$, slowly add 40 ml of 6% $CF_3COOH$ under stirring, ensure the concentration of $CF_3COOH$ in the system is 3%, and stir and react at room temperature for 30 min. Add saturated $NaHCO_3$ to neutralize the solution, separate the solution to obtain an organic phase, wash the organic phase with 30 ml of saturated $NaHCO_3$ once, dry the organic phase over anhydrous $Na_2SO_4$ and filter, concentrate and separate in a normal-pressure column the organic phase to obtain the product with a yield of 64.1%. The yield is the percentage between the weight of the product and the calculated theoretical output calculated according to OH[CC]AZMB.

(18) Synthesis of OH[ACG]AZMB

Dissolve product DMTr[ACG]AZMB obtained in step (12) in 20 ml of $CH_2Cl_2$, slowly add 20 ml of 6% $CF_3COOH$ under stirring, ensure the concentration of $CF_3COOH$ in the system is 3%, and stir and react at room temperature for 10 min. Add saturated $NaHCO_3$ to neutralize the solution, separate the solution to obtain an organic phase, wash the organic phase with 15 ml of saturated $NaHCO_3$ once, dry the organic phase over anhydrous $Na_2SO_4$ and filter, concentrate and separate in a normal-pressure column the organic phase to obtain 2.0 g of the product with a yield of 55. %. The yield is the percentage between the weight of the product and the calculated theoretical output calculated according to HO[CG]AZMB.

(19) Synthesis of OH[GAU]AZMB

Add the product of synthesis example 5 (3.82 g, 3.69 mmol) and OH[AU]AZMB (3.30 g, 2.80 mmol) obtained in step (3) into a 100 ml round bottom flask, add 20 ml of anhydrous pyridine to dissolve the sample, add MSNT (2.33 g, 7.84 mmol) by three times and stir it at room temperature 4 h. Add 5 ml of 1M TEAB, stir 30 min to terminate the reaction, pour the reaction solution into 100 ml of $CH_2Cl_2$, wash it with 1M TEAB three times (20 ml each time), separate the solution to obtain an organic phase, dry the organic phase over $Na_2SO_4$ and filter, concentrate and separate in a normal-pressure column the organic phase to obtain the product. Dissolve the obtained product in 40 ml of $CH_2Cl_2$, slowly add 40 ml of 6% $CF_3COOH$ under stirring, ensure the concentration of $CF_3COOH$ in the system is 3%, and stir and react at room temperature 30 min. Add saturated $NaHCO_3$ to neutralize the solution, separate the solution to obtain an organic phase, wash the organic phase with 30 ml of saturated $NaHCO_3$ once, dry the organic phase over anhydrous $Na_2SO_4$ and filter, concentrate and separate in a normal-pressure column the organic phase to obtain the product with a yield of 63%. The yield is the percentage between the weight of the product and the calculated theoretical output calculated according to OH[AU]AZMB.

(20) Synthesis of OH[AGG]AZMB

Add the product of synthesis example 1 (3.30 g, 3.10 mmol) and OH[GG]AZMB (2.98 g, 2.35 mmol) obtained in step (2) into a 100 ml round bottom flask, add 15 ml of anhydrous pyridine to dissolve the sample, add MSNT (1.96 g, 6.6 mmol) by batch and stir and react at room temperature 2.5 h. Add 10 ml of 1M TEAB, stir 20 min to terminate the reaction, pour the reaction solution into 150 ml of $CH_2Cl_2$, wash it with 1M TEAB three times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 25 ml of $CH_2Cl_2$, slowly add 25 ml of 6% $CF_3COOH$ under stirring, ensure the concentration of $CF_3COOH$ in the system is 4%, and stir and react at room temperature 30 min. Add saturated $NaHCO_3$ to neutralize the solution, separate the solution to obtain an organic phase, wash the organic phase with 20 ml of saturated $NaHCO_3$ once, dry the organic phase over anhydrous $Na_2SO_4$ and filter, concentrate and separate in a normal-pressure column the organic phase to obtain the product with a yield of 69%. The yield is the percentage between the weight of the product and the calculated theoretical output calculated according to OH[GG]AZMB.

(21) Synthesis of OH[AACC]AZMB

Add the product of synthesis example 1 (3.24 g, 3.00 mmol) and OH[ACC]AZMB (4.31 g, 2.25 mmol) obtained in step (15) into a 100 ml round bottom flask, add 15 ml of anhydrous pyridine to dissolve the sample, add MSNT (1.87 g, 6.30 mmol) by batch and stir and react at room temperature for 3 h. Add 10 ml of 1M TEAB, stir for 20 min to terminate the reaction, pour the reaction solution into 100 ml of $CH_2Cl_2$, wash it with 1M TEAB three times (20 ml each time), separate the solution to obtain an organic phase, dry the organic phase over anhydrous $Na_2SO_4$ and filter, concentrate and separate in a normal-pressure column the organic phase to obtain the product. Dissolve the obtained product in 50 ml of $CH_2Cl_2$, slowly add 50 ml of 6% $CF_3COOH$ under stirring, ensure the concentration of $CF_3COOH$ in the system is 3%, and stir and react at room temperature 30 min. Add saturated $NaHCO_3$ to neutralize the solution, separate the solution to obtain an organic phase, wash the organic phase with 40 ml of saturated $NaHCO_3$ once, dry the organic phase over anhydrous $Na_2SO_4$ and filter, concentrate and separate in a normal-pressure column the organic phase to obtain the product with a yield of 50%. The yield is the percentage between the weight of the product and the calculated theoretical output calculated according to OH[ACC]AZMB.

(22) Synthesis of DMTr[CGCA]AZMB

Add the product of synthesis example 3 (3.04 g, 2.88 mmol) and OH[GCA]AZMB (4.25 g, 2.21 mmol) obtained in step (16) into a 100 ml round bottom flask, add 15 ml of anhydrous pyridine to dissolve the sample, add MSNT (1.84 g, 6.19 mmol) by three times and stir it at room temperature 3.5 h. Add 10 ml of 1M TEAB, stir 20 min to terminate the reaction, pour the reaction solution into 100 ml of $CH_2Cl_2$, wash it with 1M TEAB three times (50 ml each time), separate the solution to obtain an organic phase, dry the organic phase over anhydrous $Na_2SO_4$ and filter, concentrate and separate in a normal-pressure column the organic phase to obtain the product with a yield of 76%. The yield is the percentage between the weight of the product and the calculated theoretical output calculated according to OH[GCA]AZMB.

(23) Synthesis of DMTr[UUCC]AZMB

Add the product of synthesis example 6 (2.43 g, 2.55 mmol) and OH[UCC]AZMB (3.50 g, 1.96 mmol) obtained in step (17) into a 50 ml round bottom flask, add 15 ml of anhydrous pyridine to dissolve the sample, add MSNT (1.63 g, 5.49 ml) by three times and stir it at room temperature for 4 h. Add 10 ml of 1M TEAB, stir for 20 min to terminate the reaction, pour the reaction solution into 100 ml of $CH_2Cl_2$, wash it with 1M TEAB three times (20 ml each time), separate the solution to obtain an organic phase, dry the organic phase over anhydrous $Na_2SO_4$ and filter, concentrate and separate in a normal-pressure column the organic phase to obtain the product with a yield of 78%. The yield is the percentage between the weight of the product and the calculated theoretical output calculated according to OH[UCC]AZMB.

(24) Synthesis of DMTr[GG]OH

Add DMTr[GG]AZMB (7.55 g, 4.81 mmol) obtained in step (9) and $Ph_3P$ (5.04 g, 19.2 mmol) into a 500 ml round bottom flask, add 240 ml of dioxane/water (v:v=9:1) to dissolve the sample, stir and react at room temperature for 8 h, end the reaction, remove the solvent and conduct fast liquid chromatography by a high performance separation, purification and preparation chromatograph (model: Combiflash Companion S: manufacturer: Teledyne ISCO INC.) to obtain the crude product containing triphenylphosphine oxide and the removed 3'-protective group, dry it and keep it for future use.

(25) Synthesis of DMTr[GG]PO$^-$

Add 1,2,4-triazole (1.50 g, 22.1 mmol) and the double distilled triethylamine (3.58 g, 35.4 mmol) into a 100 ml round bottom flask, add 16.6 ml of anhydrous $CH_2Cl_2$ to dissolve it, dropwise add 2-chlorophenyl dichlorophosphate (2.17 g, 8.8 mmol) dissolved in 8.8 ml of anhydrous $CH_2Cl_2$ under the cooling condition of ice bath and stir and react 1 h. Change the ice bath into ice salt bath, adjust temperature to $-10 \sim -5$, dropwise add product DMTr[GG]OH obtained in step (24) dissolved in 13.3 ml of anhydrous $CH_2Cl_2$, and stir and react 4 h in ice salt bath. Add 20 ml of 1M TEAB, continue the stirring and reaction 0.5 h. stop the reaction, separate the solution to obtain an organic phase, wash it with 1M TEAB three times, dry the organic phase over anhydrous $Na_2SO_4$ and filter, concentrate and separate in a normal-pressure column the organic phase to obtain the product with a yield of 60%. The yield is the percentage between the weight of the product and the calculated theoretical output calculated according to DMTr[GG]AZMB.

(26) Synthesis of DMTr[UCA]OH

A method same as step (24) is adopted to synthesize DMTr[UCA]OH, except that DMTr[UCA]AZMB (11.3 g, 4.69 mmol) obtained in step (11) and $Ph_3P$ (4.96 g, 18.7 mmol) are adopted.

(27) Synthesis of DMTr[UCA]PO$^-$

A method same as step (25) is adopted to prepare DMTr[UCA]PO$^-$, except that 19.5 ml of anhydrous $CH_2Cl_2$ is used to dissolve 1,2,4-triazole (1.77 g, 26.0 mmol) and the double distilled triethylamine (4.21 g, 41.7 mmol), 10.5 ml of anhydrous $CH_2Cl_2$ is used to dissolve 2-chlorophenyl dichlorophosphate (2.56 g, 10.4 mmol) and 15.6 ml of anhydrous $CH_2Cl_2$ is used to dissolve DMTr[UCA]OH obtained in step (26). The yield is 79%. The yield is the percentage between the weight of the product and the calculated theoretical output calculated according to DMTr[UCA]AZMB.

(28) Synthesis of DMTr[UGC]OH

A method same as step (24) is adopted to synthesize DMTr[UGC]OH, except that DMTr[UGC]AZMB (10.6 g, 4.42 mmol) obtained in step (10) and $Ph_3P$ (4.63 g, 17.7 mmol) are adopted.

(29) Synthesis of DMTr[UGC]PO$^-$

A method same as step (25) is adopted to prepare DMTr[UGC]PO$^-$, except that 19.4 ml of anhydrous $CH_2Cl_2$ is used to dissolve 1,2,4-triazole (1.76 g, 25.9 mmol) and the double distilled triethylamine (4.18 g, 41.4 mmol), 10.4 ml of anhydrous $CH_2Cl_2$ is used to dissolve 2-chlorophenyl dichlorophosphate (2.54 g, 10.3 mmol) and 15.5 ml of anhydrous $CH_2Cl_2$ is used to dissolve DMTr[UGC]OH obtained in step (28). The yield is 71%. The yield is the percentage between the weight of the product and the calculated theoretical output calculated according to DMTr[UGC]AZMB.

(30) Synthesis of DMTr[GUU]OH

A method same as step (24) is adopted to synthesize DMTr[GUU]OH, except that DMTr[GUU]AZMB (5.41 g, 2.36 mmol) obtained in step (13) and $Ph_3P$ (2.47 g, 9.43 mmol) are adopted and the amount of dioxane/water (v:v=9:1) is 120 ml.

(31) Synthesis of DMTr[GUU]PO$^-$

A method same as step (25) is adopted to prepare DMTr[GUU]PO$^-$, except that 9.8 ml of anhydrous $CH_2Cl_2$ is used to dissolve 1,2,4-triazole (891 mg, 13.1 mmol) and the double distilled triethylamine (2.12 g, 21.0 mmol), 5.2 ml of anhydrous $CH_2Cl_2$ is used to dissolve 2-chlorophenyl dichlorophosphate (2.54 g, 10.3 mmol) and 7.9 ml of anhydrous $CH_2Cl_2$ is used to dissolve DMTr[GUU]OH obtained in step (30). The yield is 64%. The yield is the percentage between the weight of the product and the calculated theoretical output calculated according to DMTr[GUU]AZMB.

(32) Synthesis of DMTr[GUG]OH

A method same as step (24) is adopted to synthesize DMTr[GUG]OH, except that DMTr[GUG]AZMB (4.40 g, 1.83 mmol) obtained in step (14) and $Ph_3P$ (1.92 g, 7.33 mmol) are adopted and the amount of dioxane/water (v:v=9:1) is 900 ml.

(33) Synthesis of DMTr[GUG]PO$_-$

A method same as step (25) is adopted to prepare DMTr[GUG]PO$^-$, except that 6.8 ml of anhydrous $CH_2Cl_2$ is used to dissolve 1,2,4-triazole (622 mg, 9.15 mmol) and the double distilled triethylamine (1.48 g, 14.7 mmol), 3.6 ml of anhydrous $CH_2Cl_2$ is used to dissolve 2-chlorophenyl dichlorophosphate (898 mg, 3.66 mmol) and 5.5 ml of anhydrous $CH_2Cl_2$ is used to dissolve DMTr[GUG]OH obtained in step (32). The yield is 64%. The yield is the percentage between the weight of the product and the calculated theoretical output calculated according to DMTr[GUG]AZMB.

(34) Synthesis of DMTr[CGCA]OH

A method same as step (24) is adopted to synthesize DMTr[CGCA]OH, except that DMTr[CGCA]AZMB (4.77 g, 1.67 mmol) obtained in step (22) and $Ph_3P$ (1.74 g, 6.66 mmol) are adopted.

(35) Synthesis of DMTr[CGCA]PO$^-$

A method same as step (25) is adopted to prepare DMTr[CGCA]PO$^-$, except that 10.0 ml of anhydrous $CH_2Cl_2$ is used to dissolve 1,2,4-triazole (604 mg, 8.88 mmol) and the double distilled triethylamine (1.62 g, 16.0 mmol), 3.5 ml of anhydrous $CH_2Cl_2$ is used to dissolve 2-chlorophenyl dichlorophosphate (873 mg, 3.55 mmol) and 5.4 ml of anhydrous $CH_2Cl_2$ is used to dissolve DMTr[CGCA]OH obtained in step (34). The yield is 64%. The yield is the percentage between the weight of the product and the calculated theoretical output calculated according to DMTr[GUU]AZMB.

(36) Synthesis of DMTr[UUCC]OH

A method same as step (24) is adopted to synthesize DMTr[UUCC]OH, except that DMTr[UUCC]AZMB (3.85 g, 1.19 mmol) obtained in step (23) and Ph$_3$P (1.25 g, 4.77 mmol) are adopted and the amount of dioxane/water (v:v=9:1) mixed solution is 60 ml.

(37) Synthesis of DMTr[UUCC]PO$^-$

A method same as step (25) is adopted to prepare DMTr[UUCC]PO$^-$, except that 9.8 ml of anhydrous CH$_2$Cl$_2$ is used to dissolve 1,2,4-triazole (891 mg, 13.1 mmol) and the double distilled triethylamine (2.12 g, 21.0 mmol), 5.2 ml of anhydrous CH$_2$Cl$_2$ is used to dissolve 2-chlorophenyl dichlorophosphate (1.29 g, 5.25 mmol) and 5.5 ml of anhydrous CH$_2$Cl$_2$ is used to dissolve DMTr[UUCC]OH obtained in step (36). The yield is 86%. The yield is the percentage between the weight of the product and the calculated theoretical output calculated according to DMTr[UUCC]AZMB.

(38) Synthesis of DMTr[GGAACC]AZMB

Add DMTr[GG]PO$^-$ (2.74 g, 2.15 mmol) obtained in step (25) and HO[AACC]AZMB (2.70 g, 1.05 mmol) obtained in step (21) into a 100 ml round bottom flask, add 10 ml of anhydrous pyridine to fully dissolve them, add MSNT (0.873 g, 2.94 mmol) by batch, react at room temperature for 3 h, add 1 ml of 1M TEAB, stir 25 min, stop the reaction, pour the solution into about 100 ml of CH$_2$Cl$_2$, wash it with 1M TEAB three times, separate the solution to obtain an organic phase, dry the organic phase over anhydrous Na$_2$SO$_4$ and filter, concentrate and separate in a normal-pressure column the organic phase to obtain the product with a yield of 48%.

(39) Synthesis of DMTr[UCACA]AZMB

A method same as step (38) is adopted to synthesize DMTr[UCACA]AZMB, except that DMTr[UCA]PO$^-$ (4.84 g, 2.16 mmol) obtained in step (27) and HO[CA]AZMB (2.01 g, 1.57 mmol) obtained in step (5) are adopted, the amount of anhydrous pyridine is 15 ml and MSNT (1.31 g, 4.40 mmol). The yield is 66%.

(40) Synthesis of DMTr[UCAACG]AZMB

A method same as step (38) is adopted to synthesize DMTr[UCAACG]AZMB, except that DMTr[UCA]PO$^-$ (4.56 g, 2.03 mmol) obtained in step (27) and HO[ACG]AZMB (2.70 g, 1.41 mmol) obtained in step (20) are adopted, the amount of anhydrous pyridine is 15 ml and MSNT (1.17 g, 3.95 mmol). The yield is 60%.

(41) Synthesis of DMTr[CGCAUU]AZMB

A method same as step (38) is adopted to synthesize DMTr[CGCAUU]AZMB, except that DMTr[CGCA]PO$^-$ (3.2 g, 1.07 mmol) obtained in step (35) and HO[UU]AZMB (1.05 g, 1.00 mmol) obtained in step (4) are adopted, the amount of anhydrous pyridine is 10 ml and MSNT (832 mg, 2.80 mmol). The yield is 87%.

(42) Synthesis of DMTr[UGCGC]AZMB

A method same as step (38) is adopted to synthesize DMTr[UGCGC]AZMB, except that DMTr[UGC]PO$^-$ (7.00 g, 3.14 mmol) obtained in step (29) and HO[GC]AZMB (3.10 g, 2.46 mmol) obtained in step (7) are adopted, the amount of anhydrous pyridine is 25 ml and MSNT (2.05 g, 6.89 mmol). The yield is 78%.

(43) Synthesis of DMTr[GUUGAU]AZMB

A method same as step (38) is adopted to synthesize DMTr[GUUGAU]AZMB, except that DMTr[GUU]PO$^-$ (3.20 g, 1.51 mmol) obtained in step (31) and HO[GAU]AZMB (2.30 g, 1.27 mmol) obtained in step (19) are adopted, the amount of anhydrous pyridine is 12 ml and MSNT (1.06 g, 3.56 mmol). The yield is 74%.

(44) Synthesis of DMTr[GUGAGG]AZMB

A method same as step (38) is adopted to synthesize DMTr[GUGAGG]AZMB, except that DMTr[GUG]PO$^-$ (2.6 g, 1.16 mmol) obtained in step (33) and HO[AGG]AZMB (1.90 g, 0.99 mmol) obtained in step (18) are adopted, the amount of anhydrous pyridine is 10 ml and MSNT (832 mg, 2.8 mmol). The yield is 74%.

(45) Synthesis of DMTr[UUCCUU]AZMB

A method same as step (38) is adopted to synthesize DMTr[UUCCUU]AZMB, except that DMTr[UUCC]PO$^-$ (2.80 g, 1.02 mmol) obtained in step (37) and HO[U]AZMB (0.94 g, 0.90 mmol) obtained in step (4) are adopted, the amount of anhydrous pyridine is 10 ml and MSNT (748 mg, 2.52 mmol). The yield is 82%.

(46) Synthesis of HO[UCACA]AZMB

Dissolve DMTr[UCACA]AZMB (3.80 g, 1.03 mmol) obtained in step (39) in 15 ml of CH$_2$Cl$_2$, slowly add 6% CF$_3$COOH, ensure the concentration of CF$_3$COOH in the system is 4% and stir at room temperature 30 min. Add saturated NaHCO$_3$ to neutralize the solution, separate the solution to obtain an organic phase, wash the organic phase with 15 ml of saturated NaHCO$_3$ once, dry the organic phase over anhydrous Na$_2$SO$_4$ and filter, concentrate and separate in a normal-pressure column the organic phase to obtain the product with a yield of 84%.

(47) Synthesis of HO[CGCAUU]AZMB A method same as step (46) is adopted to prepare HO[CGCAUU]AZMB, except that DMTr[CGCAUU]AZMB (3.8 g, 0.97 mmol) obtained in step (41) is adopted. The yield is 58%.

(48) Synthesis of HO[GUUGAU]AZMB

A method same as step (46) is adopted to prepare HO[GUUGAU]AZMB, except that DMTr[GUUGAU]AZMB (3.50 g, 0.94 mmol) obtained in step (43) is adopted. The yield is 58%.

(49) Synthesis of HO[UUCCUU]AZMB

A method same as step (46) is adopted to prepare HO[UUCCUU]AZMB, except that DMTr[UUCCUU]AZMB (2.90 g, 0.79 mmol) obtained in step (45) is adopted. The yield is 87%.

(50) Synthesis of DMTr[GGAACC]PO$^-$

Add DMTr[GGAACC]AZMB (2.20 g, 0.50 mmol) obtained in step (38) and Ph$_3$P (524 mg, 2.00 mmol) into a 100 ml round bottom flask, add 25 ml of dioxane/water (v:v=9:1), stir and react at room temperature 18 h, remove the solvent through rotary evaporation and conduct fast liquid chromatography by a high performance separation, purification and preparation chromatograph (model: Combiflash Companion/TS; manufacturer: Teledyne ISCO INC.) to obtain 2.00 g of the crude product containing triphenylphosphine oxide and the removed 3'-protective group, dry it and keep it for future use.

Add 1,2,4-triazole (170 mg, 2.50 mmol) and the double distilled triethylamine (454 mg, 4.50 mmol) into a 100 ml round bottom flask, add 1.5 ml of anhydrous CH$_2$Cl$_2$ to dissolve them, dropwise add 2-chlorophenyl dichlorophosphate (246 mg, 1.0 mmol) dissolved in 1.0 ml of anhydrous CH$_2$Cl$_2$ under the cooling condition of ice bath and stir and react 1 h. Change the ice bath into ice salt bath, adjust temperature to −10° C.~−5° C., dropwise add product DMTr[GGAACC]OH obtained in the above step, and stir and react 4 h. Add 10 ml of 1M TEAB and continue the stirring and reaction 0.5 h. Stop the reaction, separate the solution to obtain an organic phase, wash it with 1M TEAB three times, dry the organic phase over anhydrous Na$_2$SO$_4$ and filter, concentrate and separate in a normal-pressure column the organic phase to obtain the product with 54% of total yield in the two steps.

(51) Synthesis of DMTr[UCAACG]PO⁻

A method same as step (50) is adopted to synthesize DMTr[UCAACG]PO⁻, except that DMTr[UCAACG]AZMB (3.60 g, 0.94 mmol) obtained in step (40) is adopted. The yield in the two steps is 66%.

(52) Synthesis of DMTr[UGCGC]PO⁻

A method same as step (50) is adopted to synthesize DMTr[UGCGC]PO⁻, except that DMTr[UGCGC]AZMB (6.40 g, 1.90 mmol) obtained in step (42) is adopted. The yield in the two steps is 70%.

(53) Synthesis of DMTr[GUGAGG]PO⁻

A method same as step (50) is adopted to synthesize DMTr[GUGAGG]PO⁻, except that DMTr[GGAACC]AZMB (3.00 g, 0.75 mmol) obtained in step (38) is adopted. The yield in the two steps is 41%.

(54) Synthesis of DMTr[GGAACCUCACA]AZMB (SEQ ID NO. 4)

Add DMTr[GGAACC]PO⁻ (1.2 g, 0.26 mmol) obtained in step (50) and HO[UCACA]AZMB (0.85 g, 0.25 mmol) obtained in step (46) into a 50 ml round bottom flask, add 5 ml of anhydrous pyridine to fully dissolve them, add MSNT (208 mg, 0.70 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$ and filter, concentrate and separate in a normal-pressure column the organic phase to obtain 1.40 g of the product with a yield of 71%.

(55) Synthesis of DMTr[UGCGCGUUGAU]AZMB (SEQ ID NO. 5)

Add DMTr[UGCGC]PO⁻ (2.52 g, 0.72 mmol) obtained in step (52) and HO[GUUGAU]AZMB (2.5 g, 0.71 mmol) obtained in step (486) into a 50 ml round bottom flask, add 8 ml of anhydrous pyridine to fully dissolve them, add MSNT (500 mg, 1.68 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$ and filter, concentrate and separate in a normal-pressure column the organic phase to obtain the product with a yield of 49%.

(56) Synthesis of DMTr[UCAACGCGCAUU]AZMB (SEQ ID NO. 6)

Add DMTr[UCAACG]PO⁻ (2.43 g, 0.61 mmol) obtained in step (51) and HO[CGCAUU]AZMB (1.85 g, 0.5 μmol) obtained in step (47) into a 50 ml round bottom flask, add 8 ml of anhydrous pyridine to fully dissolve them, add MSNT (424 mg, 1.43 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$, filter, concentrate and separate in a normal-pressure column the organic phase to obtain the product and directly use the product in next reaction.

(57) Synthesis of DMTr[GUGAGGUUCCUU]AZMB (SEQ ID NO. 7)

Add DMTr[GUGAGG]PO⁻ (1.40 g, 0.30 mmol) obtained in step (53) and HO[UUCCUU]AZMB (1.24 g, 0.37 mmol) obtained in step (49) into a 50 ml round bottom flask, add 6 ml of anhydrous pyridine to fully dissolve them, add MSNT (249 mg, 0.84 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$, filter, concentrate and separate in a normal-pressure column the organic phase to obtain the product and directly use the product in next reaction.

(58) Synthesis of HO[UCAACGCGCAUU]AZMB (SEQ ID NO. 6)

Dissolve DMTr[UCAACGCGCAUU]AZMB (SEQ ID NO. 6) obtained in step (56) in 10 ml of $CH_2Cl_2$, slowly add 6% $CF_3COOH$, ensure the concentration of $CF_3COOH$ in the system is 4% and stir at room temperature 30 min. Add saturated $NaHCO_3$ to neutralize the solution, separate the solution to obtain an organic phase, wash the organic phase with saturated $NaHCO_3$ once, dry the organic phase over anhydrous $Na_2SO_4$ and filter, concentrate and separate in a normal-pressure column the organic phase to obtain the product with a yield of 53%. The yield is the percentage between the weight of the product and the calculated theoretical output calculated according to HO[CGCAUU]AZMB.

(59) Synthesis of HO[GUGAGGUUCCUU]AZMB (SEQ ID NO. 7)

Dissolve DMTr[GUGAGGUUCCUU]AZMB (SEQ ID NO. 7) obtained in step (57) in 10 ml of $CH_2Cl_2$, slowly add 6% $CF_3COOH$, ensure the concentration of $CF_3COOH$ in the system is 4% and stir at room temperature 30 min. Add saturated $NaHCO_3$ to neutralize the solution, separate the solution to obtain an organic phase, wash the organic phase with saturated $NaHCO_3$ once, dry the organic phase over anhydrous $Na_2SO_4$ and filter, concentrate and separate in a normal-pressure column the organic phase to obtain the product with a yield of 54%. The yield is the percentage between the weight of the product and the calculated theoretical output calculated according to HO[UUCCUU]AZMB.

(60) Synthesis of DMTr[GGAACCUCACA]PO⁻ (SEQ ID NO. 4)

Add DMTr[GGAACCUCACA]AZMB (SEQ ID NO. 4) (1.40 g, 0.18 mmol) obtained in step (54) and $Ph_3P$ (200 mg, 0.76 mmol) into a 100 ml round bottom flask, add 10 ml of dioxane/water (v:v=9:1) to dissolve them, stir and react at room temperature 28 h, remove the solvent through rotary evaporation, conduct fast liquid chromatography by a high performance separation, purification and preparation chromatograph to obtain 1.2 g of crude product containing triphenylphosphine oxide and the removed 3'-protective group, dry it and keep it for future use.

Add 1,2,4-triazole (65 mg, 0.96 mmol) and the double distilled triethylamine (162 mg, 1.60 mmol) into a 25 ml round bottom flask, add 0.5 ml of anhydrous $CH_2Cl_2$ to dissolve them, dropwise add 2-chlorophenyl dichlorophosphate (98 mg, 0.40 mmol) dissolved in 0.5 ml of anhydrous $CH_2Cl_2$ under the cooling condition of ice bath and stir and react 1 h. Change the ice bath into ice salt bath, adjust temperature to −10° C.~−5° C., dropwise add product DMTr[GGAACCUCACA]OH (SEQ ID NO. 4) obtained in the above step, and stir and react 5.5 h. Add 3 ml of 1M TEAB and continue the stirring and reaction 1 h. Separate the solution to obtain an organic phase, wash it with 1M TEAB three times, dry the organic phase over anhydrous $Na_2SO_4$ and filter, concentrate and separate in a normal-pressure column the organic phase to obtain the product with a yield of 43%. The yield is the percentage between the weight of the product and the calculated theoretical output calculated according to DMTr[GGAACCUCACA]AZMB (SEQ ID NO. 4).

(61) Synthesis of DMTr[UGCGCGUUGAU]PO⁻ (SEQ ID NO. 5)

Add DMTr[UGCGCGUUGAU]AZMB (SEQ ID NO. 5) (1.95 g, 0.28 mmol) obtained in step (55) and $Ph_3P$ (350 mg, 1.34 mmol) into a 100 ml round bottom flask, add 10 ml of dioxane/water (v:v=9:1) to dissolve the sample, stir and react at room temperature 28 h, end the reaction, remove the solvent through rotary evaporation, conduct fast liquid chromatography by a high performance separation, purification and preparation chromatograph to obtain 1.45 g of crude product containing triphenylphosphine oxide and the removed 3'-protective group, dry it and keep it for future use.

Add 1,2,4-triazole (90 mg, 1.32 mmol) and the double distilled triethylamine (224 mg, 2.22 mmol) into a 100 ml round bottom flask, add 1.0 ml of anhydrous $CH_2Cl_2$ to dissolve the sample, dropwise add 2-chlorophenyl dichlorophosphate (137 mg, 0.56 mmol) dissolved in 0.5 ml of anhydrous $CH_2Cl_2$ under the cooling condition of ice bath and stir and react 1 h. Change the ice bath into ice salt bath, adjust temperature to −10° C.~−5° C., dropwise add product DMTr[UGCGCGUUGAU]OH (SEQ ID NO. 5) obtained in the above step and dissolved in anhydrous $CH_2Cl_2$, and stir and react 5.5 h. Add 3 ml of 1M TEAB and continue the stirring and reaction 1 h. Stop the reaction, separate the solution to obtain an organic phase, wash it with 1M TEAB three times, dry the organic phase over anhydrous $Na_2SO_4$ and filter, concentrate and separate in a normal-pressure column the organic phase to obtain the product with a yield of 34.4%. The yield is the percentage between the weight of the product and the calculated theoretical output calculated according to DMTr[UGCGCGUUGAU]AZMB (SEQ ID NO. 5).

(62) Synthesis of DMTr[GGAACCUCACAUCAACGCGCAUU]AZMB (SEQ ID NO. 3) Add DMTr[GGAACCUCACA]PO⁻ (SEQ ID NO. 4) (560 mg, 70 mmol) obtained in step (60) and HO[UCAACGCGCAUU]AZMB (SEQ ID NO. 6) (500 mg, 70 mmol) obtained in step (58) into a 25 ml round bottom flask, add 1.5 ml of anhydrous pyridine to fully dissolve the sample, add MSNT (62 mg, 0.21 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$ and filter, concentrate and separate in a normal-pressure column the organic phase to obtain the product with a yield of 96%.

(63) Synthesis of DMTr[UGCGCGUUGAUGUGAGGUUCCUU]AZMB (SEQ ID NO. 2)

Add DMTr[UGCGCGUUGAU]PO⁻ (SEQ ID NO. 5) (560 mg, 79 umol) obtained in step (61) and HO[GUGAGGUUCCUU]AZMB (SEQ ID NO. 7) (600 mg, 79 umol) obtained in step (59) into a 25 ml round bottom flask, add 1.5 ml of anhydrous pyridine to fully dissolve the sample, add MSNT (70 mg, 0.24 mmol) by batch and react at room temperature 8 h. Add 1 ml of 1M TEAB, stir 25 min, stop the reaction, pour the reaction solution into about 50 ml of $CH_2Cl_2$, wash it with 1M TEAB three times, separate the solution to obtain an organic phase, dry the organic phase over anhydrous $Na_2SO_4$ and filter, concentrate and separate in a normal-pressure column the organic phase to obtain the product with a yield of 88%.

Example 4

This example synthesizes oligonucleotides.

```
Synthesis target:
                                        (SEQ ID NO. 3)
5'-GGAACCUCACAUCAACGCGCAUU-3'
And
                                        (SEQ ID NO. 2)
5'-UGCGCGUUGAUGUGAGGUUCCUU-3'
```

The protective groups are removed by a method same as that in Example 2, except that DMTr[GGAACCUCACAUCAACGCGCAUU]AZMB (SEQ ID NO. 3) and DMTr[UGCGCGUUGAUGUGAG GUUCCUU]AZMB substitutes DMTr[CGAAAGAACG]AZMB (SEQ ID NO. 1) synthesized in Example 3 are used, respectively.

As a result of sequencing, the prepared sequences are consistent with the designed sequences.

What is claimed is:

1. A method for preparing an oligonucleotide, comprising reacting the compound represented by Formula (1) with the compound represented by Formula (2) in a liquid reaction medium under the condition of condensation reaction to obtain the compound represented by Formula (3), wherein 1-(2-mesitylenesulfonyl)-3-nitro-1H-1,2,4-triazole (MSNT) is applied as condensing agent,

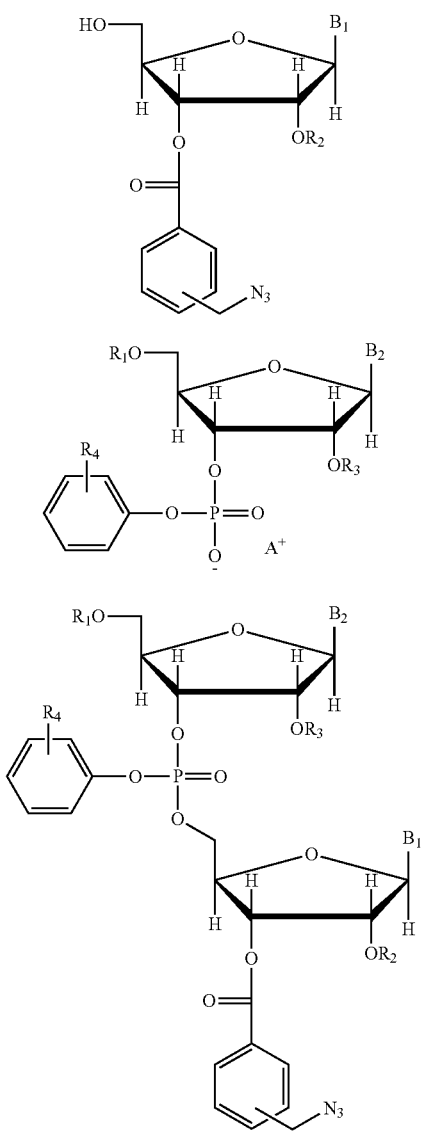

Formula (1)

Formula (2)

Formula (3)

and wherein: $R_1$ represents 4,4'-dimethoxytriphenylmethyl, or a covalently attached 5'-substituent derived from RNA or from DNA;

$R_2$ and $R_3$ independently represent a sterically hindered trisubstituted silyl protective group;

$R_4$ represents a halogen atom;

$A^+$ represents a tri-alkyl ammonium ion;

$B_1$ and $B_2$ independently represent 9-guaninyl substituted with N-acyl, 9-adeninyl substituted with N-acyl, 1 cytosinyl substituted with N-acyl, 1-thyminyl or 1-uracilyl;

and with the proviso that in Formula (1) or (3), —CH$_2$—N$_3$ is at an ortho-position.

2. The method as in claim 1, wherein the condition of the condensation reaction comprises: the reaction medium is pyridine; relative to 1 mol of the compound represented by Formula (1), the amount of the compound represented by Formula (2) is 0.8-3 mol, the amount of the condensing agent is 2-5 mol, and the amount of the reaction medium is 5-50 L; the reaction temperature is 10-50° C. and the reaction time is 0.5-10 h.

3. The method as in claim 1, wherein $R_2$ and $R_3$ independently represent tert-butyl dimethyl silyl, phenyl dimethyl silyl, tert-butyl diphenyl silyl or triisopropyl silyl; $R_4$ represents Cl or Br; each of the alkyl groups in the tri-alkyl ammonium ion has 1-6 carbon atoms; the acyl is benzoyl, isobutyryl or acetyl.

4. The method as in claim 1, wherein in Formula (2) or (3), $R_4$ is at the ortho-position.

5. The method as in claim 1 further comprising wherein the compound represented by Formula (1) is prepared by reacting the compound represented by Formula (4) with the compound represented by Formula (5) under the condition of condensation reaction, and then followed by hydrolytic removal of the 5'-protective group, N-methyl imidazole is applied as an adjuvant;

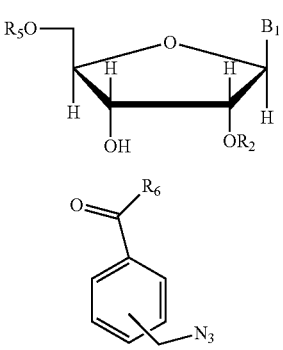

Formula (4)

Formula (5)

Where where: $R_2$ represents a sterically hindered trisubstituted silyl protective group;

$R_5$ represents 4,4'-dimethoxytriphenylmethyl;

$R_6$ represents a halogen atom;

$B_1$ represents 9-guaninyl substituted with N-acyl, 9-adeninyl substituted with N-acyl, 1-cytosinyl substituted with N-acyl, 1-thyminyl or 1-uracilyl;

and with the proviso that in Formula (5), —CH$_2$—N$_3$ is at an ortho-position.

6. The method as in claim 5, wherein the condition of the condensation reaction further comprises: one or more of dichloromethane and pyridine is applied as reaction medium; relative to 1 mol of the compound represented by Formula (4), the amount of the compound represented by Formula (5) is 1-5 mol, the amount of the adjuvant is 1.8-3.5 mol, and the amount of the reaction medium is 20-200 L; the reaction temperature is −10° C.~10° C. and the reaction time is 5-100 h.

7. The method as in claim 5, wherein the process for preparing the compound represented by Formula (5) further comprises the following steps:

(1) in the presence of benzoyl peroxide, the compound represented by Formula (9) reacts with N-halogenated succinimide to obtain the compound represented by Formula (10);

(2) the compound represented by Formula (10) reacts with alkali metal azide to obtain the compound represented by Formula (11);

(3) the compound represented by Formula (11) is hydrolyzed and acylated to obtain the compound represented by Formula (5),

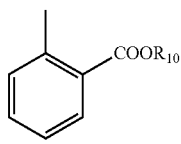
Formula (9)

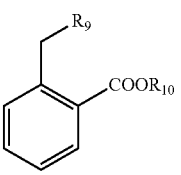
Formula (10)

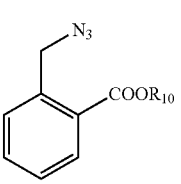
Formula (11)

Where where: $R_9$ represents a halogen atom; $R_{10}$ represents $C_1$-$C_4$ alkyl.

8. The method as in claim 7, wherein in step (1), the reaction medium is one or more of carbon tetrachloride, chloroform, benzene, toluene and heptane; relative to 1 mol of the compound represented by Formula (9), the amount of N-halogenated succinimide is 1-3 mol, the amount of benzoyl peroxide is 0.01-0.1 mol, the amount of the reaction medium is 5-20 L; the reaction temperature is 80~120° C. and the reaction time is 0.5-6 h;

in step (2), the reaction medium is one or more of ethanol, acetone, N,N-dimethyl formamide and dimethyl sulfoxide; relative to 1 mol of the compound represented by Formula (10), the amount of alkali metal azide is 1-3 mol, the amount of the reaction medium is 3-10 L; the reaction temperature is 0° C.~80° C. and the reaction time is 2-30 h;

in step (3), the hydrolysis comprises the reaction between the compound represented by Formula (11) and the alcohol-water mixed solution of alkali metal hydroxide wherein relative to 1 mol of the compound represented by Formula (10), the amount of alkali metal hydroxide is 5-100 mol, the reaction temperature is 0° C.~50° C., the reaction time is 0.1-2 h and the concentration of alkali metal hydroxide in the alcohol-water mixed solution is 5-10 wt %.

9. The method as in claim 1, further comprising wherein the compound represented by Formula (2) is obtained through the reaction of the compound represented by Formula (6), the compound represented by Formula (7) and trialkyl amine in a reaction medium in the presence of a catalyst, the catalyst being one or more of 1,2,4-triazole, triethylamine and pyridine, the reaction medium being one or more of dichloromethane, dioxane and tetrahydrofuran,

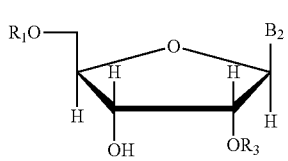
Formula (6)

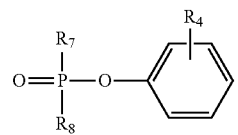
Formula (7)

where: $R_1$ represents 4,4' dimethoxytriphenylmethyl, or a covalently attached 5'-substituent derived from RNA or from DNA;

$R_3$ represents a sterically hindered trisubstituted silyl protective group;

$R_4$, $R_7$ and $R_8$ independently represent a halogen atom;

$B_2$ represents 9-guaninyl substituted with N-acyl, 9-adeninyl substituted with N-acyl, 1-cytosinyl substituted with N-acyl, 1-thyminyl or 1-uracilyl.

10. The method as in claim 9 further comprising wherein the temperature of the reaction is −10° C.~10° C. and the reaction time is 0.5-10 h; relative to 1 mol of the compound represented by Formula (6), the amount of the compound represented by Formula (7) is 1-5 mol, the amount of trialkyl amine is 1-50 mol and the amount of catalyst is 2-10 mol.

11. The method as in claim 6, wherein the process for preparing the compound represented by Formula (5) further comprises the following steps:

(1) in the presence of benzoyl peroxide, the compound represented by Formula (9) reacts with N-halogenated succinimide to obtain the compound represented by Formula (10);

(2) the compound represented by Formula (10) reacts with alkali metal azide to obtain the compound represented by Formula (11);

(3) the compound represented by Formula (11) is hydrolyzed and acylated to obtain the compound represented by Formula (5),

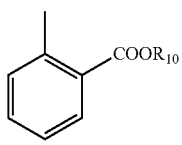
Formula (9)

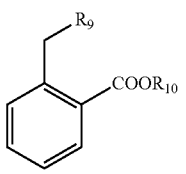
Formula (10)

Formula (11)

where: $R_9$ represents a halogen atom; $R_{10}$ represents $C_1$-$C_4$ alkyl.

* * * * *

SEQUENCE LISTING

<160> NUMBER OF SEQ ID NOS: 7

<210> SEQ ID NO 1
<211> LENGTH: 10
<212> TYPE: RNA
<213> ORGANISM: Artificial
<220> FEATURE:
<223> OTHER INFORMATION: The sequence is synthesized

<400> SEQUENCE: 1
cgaaagaacg                                                          10

<210> SEQ ID NO 2
<211> LENGTH: 23
<212> TYPE: RNA
<213> ORGANISM: Artificial
<220> FEATURE:
<223> OTHER INFORMATION: The sequence is synthesized

<400> SEQUENCE: 2
ugcgcguuga ugugagguuc cuu                                           23

<210> SEQ ID NO 3
<211> LENGTH: 23

```
<212> TYPE: RNA
<213> ORGANISM: Artificial
<220> FEATURE:
<223> OTHER INFORMATION: The sequence is synthesized

<400> SEQUENCE: 3
ggaaccucac aucaacgcgc auu                                           23

<210> SEQ ID NO 4
<211> LENGTH: 11
<212> TYPE: RNA
<213> ORGANISM: Artificial
<220> FEATURE:
<223> OTHER INFORMATION: The sequence is synthesized

<400> SEQUENCE: 4
ggaaccucac a                                                        11

<210> SEQ ID NO 5
<211> LENGTH: 11
<212> TYPE: RNA
<213> ORGANISM: Artificial
<220> FEATURE:
<223> OTHER INFORMATION: The sequence is synthesized

<400> SEQUENCE: 5
ugcgcguuga u                                                        11

<210> SEQ ID NO 6
<211> LENGTH: 12
<212> TYPE: RNA
<213> ORGANISM: Artificial
<220> FEATURE:
<223> OTHER INFORMATION: The sequence is synthesized

<400> SEQUENCE: 6
ucaacgcgca uu                                                       12

<210> SEQ ID NO 7
<211> LENGTH: 12
<212> TYPE: RNA
<213> ORGANISM: Artificial
<220> FEATURE:
<223> OTHER INFORMATION: The sequence is synthesized

<400> SEQUENCE: 7
gugagguucc uu                                                       12
```